(12) United States Patent
Javanmard et al.

(10) Patent No.: US 10,670,580 B2
(45) Date of Patent: Jun. 2, 2020

(54) QUANTIFICATION OF INFLAMMATORY MOLECULES IN EXHALED BREATH CONDENSATE USING DIFFERENTIAL PULSE VOLTAMMETRY ON REDUCED GRAPHENE OXIDE SENSOR

(71) Applicant: Rutgers, The State University of New Jersey, New Brunswick, NJ (US)

(72) Inventors: Mehdi Javanmard, West Windsor, NJ (US); Azam Gholizadeh, Piscataway, NJ (US); Manish Chhowalla, Highland Park, NJ (US); Robert J. Laumbach, Fanwood, NJ (US); Howard M. Kipen, Basking Ridge, NJ (US); Clifford P. Weisel, Teaneck, NJ (US); Andrew J. Gow, Princeton, NJ (US); Damien Voiry, Montpellier (FR)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 93 days.

(21) Appl. No.: 15/997,598

(22) Filed: Jun. 4, 2018

(65) Prior Publication Data

US 2018/0348201 A1    Dec. 6, 2018

Related U.S. Application Data

(60) Provisional application No. 62/515,244, filed on Jun. 5, 2017.

(51) Int. Cl.
G01N 33/497    (2006.01)
H01M 8/00    (2016.01)
(Continued)

(52) U.S. Cl.
CPC .......... *G01N 33/497* (2013.01); *A61B 5/082* (2013.01); *A61B 5/097* (2013.01); *A61B 5/411* (2013.01);
(Continued)

(58) Field of Classification Search
CPC .............................. H01M 8/00; G01N 33/497
See application file for complete search history.

(56) References Cited

FOREIGN PATENT DOCUMENTS

| CN | 104634848 A | 5/2015 |
|---|---|---|
| CN | 105758905 A | 7/2016 |
| KR | 20160045649 | 4/2016 |

OTHER PUBLICATIONS

Galstyan et al. ("A composite structure based on reduced graphene oxide and metal oxide nanomaterials for chemical sensors" Galstyan, V.; Comini, E.; Kholmanov, I.; Ponzoni, A.; Sberveglieri, V.; Poli, N.; Faglia, G.; Sberveglieri, G. Beilstein J. Nanotechnol. 2016, 7, 1421-1427, Oct. 2016.*

(Continued)

*Primary Examiner* — Jacob B Marks
(74) *Attorney, Agent, or Firm* — Hamilton, Brook, Smith & Reynolds, P.C.

(57) ABSTRACT

A device for detecting a biomarker for inflammation in a respiratory system includes a sample collection and/or holding area to receive an exhaled breath condensate (EBC) sample obtained from a respiratory system; an electrode system coupled to the sample collection area, the electrode system including reduced graphene oxide (rGO); and circuitry coupled to the electrode system. The circuitry is configured to apply a voltage to the EBC sample in the sample collection area via the electrode system and to measure a current via the electrode system in response to the voltage applied, in order to determine a concentration of nitrite in the EBC sample based on the current measured.

(Continued)

The concentration of nitrite is a biomarker for inflammation in the respiratory system.

20 Claims, 21 Drawing Sheets
(12 of 21 Drawing Sheet(s) Filed in Color)

(51) Int. Cl.
    *A61B 5/08*     (2006.01)
    *A61B 5/097*     (2006.01)
    *A61M 16/08*     (2006.01)
    *G01N 27/48*     (2006.01)
    *A61B 5/00*     (2006.01)

(52) U.S. Cl.
    CPC ......... *A61M 16/0808* (2013.01); *G01N 27/48* (2013.01); *A61M 2205/3303* (2013.01); *G01N 2800/122* (2013.01)

(56) References Cited

OTHER PUBLICATIONS

Robroeks, et.al., "Exhaled nitric oxide and biomarkers in exhaled breath condensate indicate the presence, severity and control of childhood asthma," Clin. Exp. Allergy Sept; 37(9):1303-11(2007).

Cherot-Komobis et.al., "Analysis of nitrogen oxide (NOx) in the exhaled breath condensate (EBC) of subjects with asthma as a complement of exhaled nitric oxide (FeNO) measurements: a cross-sectional study," BMC Research Notes 4:202 (2011).

Vijayaraj et.al., "A sensitive and selective nitrite detection in water using graphene/platinum nanocomposite," Eletroanalysis 29:345-351 (2017).

Carpagnano, GE., et al. "Exhaled markers in the monitoring of airways inflammation and its response to steroid's treatment in mild persistent asthma," Eur J Pharmacol, vol. 519, Issues 1-2, pp. 175-181 (2005).

Jiang, J., et al., "Nitrite electrochemical biosensing based on coupled graphene and gold nanoparticles," Biosens and Bioelectronics, 51,343 (2014).

Gholizadeh, Azam, et al. "Toward point-of-care management of chronic respiratory conditions: Electrochemical sensing of nitrite content in exhaled breath condensate using reduced graphene oxide," Microsystems & Nanoengineering, 3,17022; 8 pages, doi:10.1038/micronano (May 22, 2017).

"Exhaled Nitric Oxide and Exhaled Breath Condensate," https://www.wellmark.com/Provider/MedpoliciesAndAuthorizations/MedicalPolicies/polici . . . , 12 pages [retrieved on Jun. 2, 2017].

Gholizadeh, Azam, et al., entitled "Measurement of nitrite levels in exhaled breath condensate samples using electrochemically reduced graphene oxide based sensor," (poster) Jun. 5, 2016.

\* cited by examiner

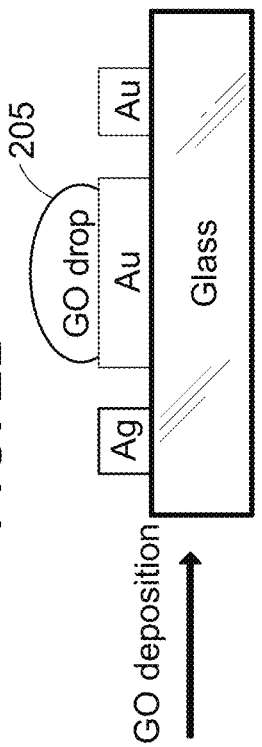
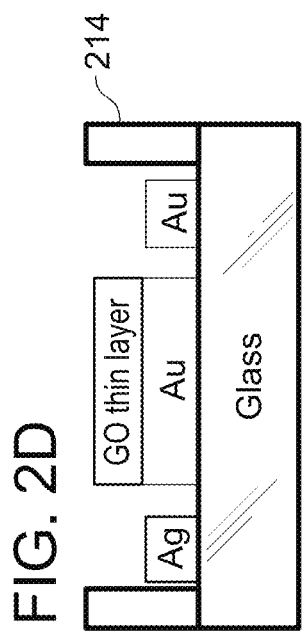
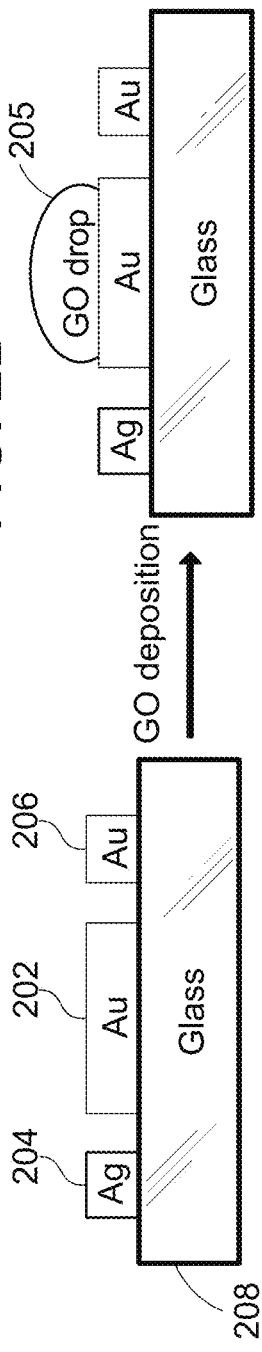
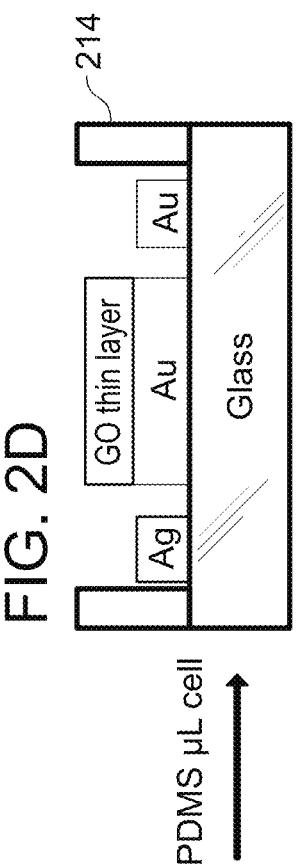
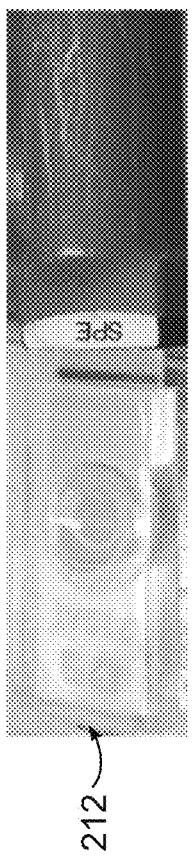
FIG. 2A
FIG. 2B
FIG. 2C
FIG. 2D
FIG. 2E Apply voltage;
measure current;

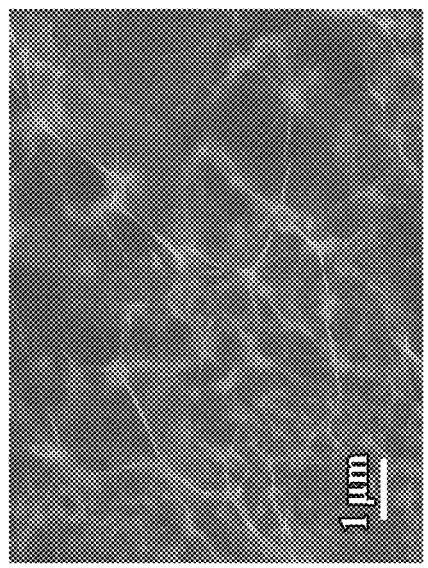
FIG. 9A
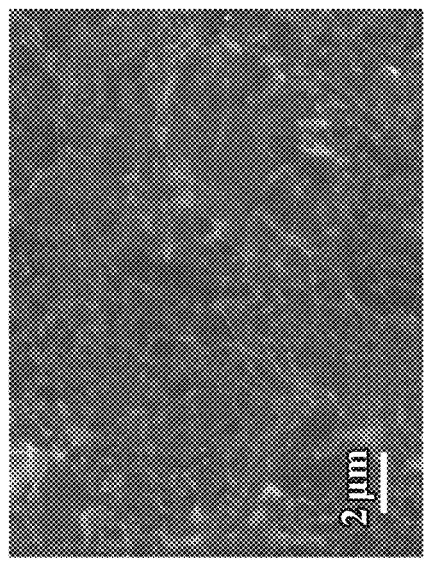
FIG. 9B
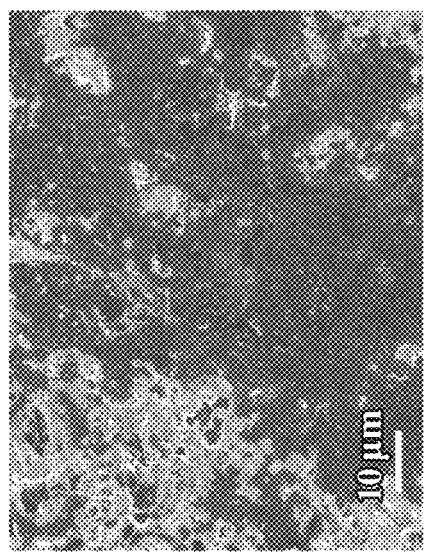
FIG. 9C
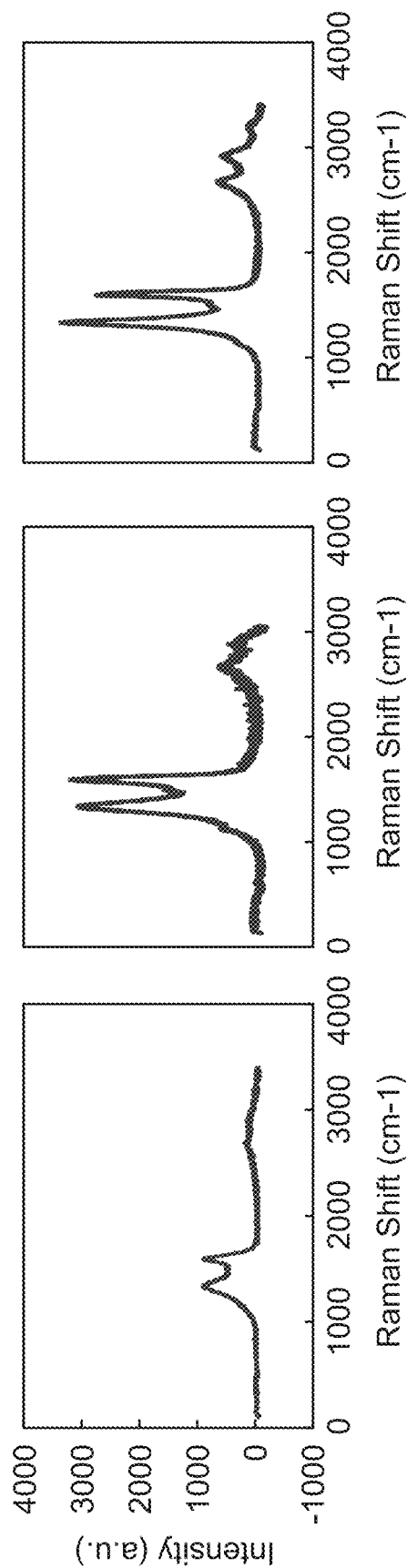
FIG. 9D
FIG. 9E
FIG. 9F

QUANTIFICATION OF INFLAMMATORY MOLECULES IN EXHALED BREATH CONDENSATE USING DIFFERENTIAL PULSE VOLTAMMETRY ON REDUCED GRAPHENE OXIDE SENSOR

RELATED APPLICATION

This application claims the benefit of U.S. Provisional Application No. 62/515,244, filed on Jun. 5, 2017. The entire teachings of the above application are incorporated herein by reference.

GOVERNMENT SUPPORT

This invention was made with government support under Grant No. ES005022 from the National Institutes of Health. The government has certain rights in the invention.

BACKGROUND

Asthma, which is characterized by variable airway inflammation and air flow obstruction, is an increasingly important global health problem. In the United States alone, ~17.7 million adults and 6.3 million children were diagnosed with asthma in 2014. Furthermore, the cost of asthma care in the United States was estimated to be $56 billion in 2007. The currently available non-invasive methods for diagnosing and monitoring asthma, i.e., spirometry and the measurement of exhaled nitric oxide, are limited by low sensitivity and the need for expensive and bulky equipment. Moreover, existing tests have a limited ability to characterize the nature and extent of underlying airway inflammation, which is widely variable between individuals.

SUMMARY

A device for detecting a biomarker for inflammation in a respiratory system includes a sample collection area to receive an exhaled breath condensate (EBC) sample obtained from a respiratory system; an electrode system coupled to the sample collection area, the electrode system including reduced graphene oxide (rGO); and circuitry coupled to the electrode system. The circuitry is configured to apply a voltage to the EBC sample in the sample collection area via the electrode system and to measure a current via the electrode system in response to the voltage applied, in order to determine a concentration of nitrite in the EBC sample based on the current measured. The concentration of nitrite is a biomarker for inflammation in the respiratory system.

The sample collection area of the device can be configured to receive an EBC sample collected, previously or concurrently, using any known technique, such as by use of a condenser (see, e.g., FIG. 1). For example, a suitable condenser can be coupled to or integrated into the device. Alternatively or in addition, the sample collection area can be configured to directly receive (e.g., collect) an EBC sample from a subject. In an embodiment of the device that is portable, a subject may breathe directly onto the sample collection area (or into a tube or other collection element in fluid communication with the sample collection area).

The sample collection area and the electrode system can form a micro-electrochemical cell defining a small volume area to hold the EBC sample. A structural layer can be positioned adjacent the electrode system, where the structural layer defines a boundary of the small volume area. The structural layer can be fabricated from PDMS.

The electrode system can include a working electrode, a counter electrode, and a reference electrode. The working electrode can include the rGO. The working electrode, the counter electrode, and the reference electrode can be screen printed on a substrate.

The working electrode can be formed using a modified drop cast method, wherein the method includes the steps of: depositing a drop of graphene oxide (GO) solution on a surface of a metal electrode, forming the drop of GO into a layer of GO on the surface of the metal electrode, and electrochemically reducing the layer of GO to form a layer of rGO. Advantageously, a glass slide can be used to form a thin GO layer without agglomeration. A spin coated GO layer may also be used.

The voltage applied by the circuitry can be a time-varying voltage having an amplitude pattern suitable for at least one of cyclic voltammetry, square wave voltammetry, and differential pulse voltammetry.

The concentration of nitrite in the EBC sample can be determined by assessing a peak value in the current measured relative to calibration data. The peak value can be assessed at a specific potential (e.g., specific redox potential) of about 0.7 Volts.

The device can further include a processor in communication with the circuitry and a memory storage, which may be integrated into the device or be remote memory storage. Communication with the processor can be wireless, e.g., via Bluetooth or other wireless communication protocols. The processor can be configured to retrieve the calibration data from the memory storage and to calculate the concentration of nitrite based on the current measured and the calibration data retrieved from the memory storage.

The respiratory system can be of a mammalian subject, in which case the device can further include an output display unit that is responsive to the determined concentration of nitrite. The output display can be configured to generate an indication that the subject is asthmatic at threshold concentration levels of the determined concentration of nitrite.

The EBC sample is one or more of a label-free, probe-free, enzyme-free and catalyst-free sample.

Elements of the device, such as one or more of the sample collection area, the electrode system, the circuitry, and the processor, can be integrated in a sensor chip. In one example, the size of the sensor chip is about 1 cm in width, about 3 cm or less in length, and about 0.5 cm in thickness (height).

The device may include a custom designed integrated circuit (CMOS chip), which may have dimensions of about 1 cm×2 cm. Any or all of the elements of the device can be implemented in the custom designed integrated circuit. The device can include an I/O interface, a display, or both. A power source (e.g., small battery) may be integrated into the device to power the integrated circuit and display, if present. In an embodiment, the weight of the device can be in the range of about 80 g to about 200 g.

In one example, the sensor chip can be a strip that plugs into a bracelet to be worn by a subject from which the EBC sample(s) is to be obtained. The bracelet may communicate wireless with other devices, such as a smart phone or other portable device, or with a monitoring station.

The device may include other sensors, such as environmental sensors to sense temperature, illumination, humidity, and pressure, or bio-sensors, such as sensors to sense skin temperature, motion, heart-rate, impedance, etc., and may include combinations of such sensors.

A method for detecting a biomarker for inflammation in a respiratory system includes receiving an exhaled breath condensate (EBC) sample in a sample collection area, the EBC sample obtained from a respiratory system; applying a voltage to the EBC sample via an electrode system coupled to the sample collection area, the electrode system including reduced graphene oxide (rGO); measuring a current via the electrode system in response to the voltage applied; and determining a concentration of nitrite in the EBC sample based on the current measured, the concentration of nitrite being a biomarker for inflammation in the respiratory system.

Embodiments of the present invention have many advantages and include technical distinguishing features such as portability, ease of use, enhanced specificity and sensitivity, and stability of nitrite as a biomarker, among others.

Embodiments can be portable (miniaturized). The test well (e.g., sample collection area) can be configured to hold an EBC sample of sufficient size (volume) to perform the assay. In a particular embodiment, the test well (e.g., sample collection area) holds about 100 µl of EBC sample. Smaller samples, e.g., 10-20 µl of EBC, may also be used. The sample well can be circular in shape and can have a diameter of 2 mm.

Embodiments can include or be implemented in a one-step process (sampling, nitrite detection) without a need to pretreat EBC samples. Embodiments can detect nitrite content at a specific potential of about 0.7 V in real time without interference from other compounds.

In contrast to exhaled NO testing, which lacks specificity and sensitivity (and insurance company may not reimburse for such testing) due to the transient nature of NO, sensing nitrite can be more reliable because nitrite is more stable. Nitrite level in EBC may represent a better biomarker for inflammatory diseases of the respiratory tract linings.

A novel electrochemical assay has been developed capable of monitoring inflammation in inner lining of respiratory airway by detecting biomarkers in exhaled breath condensate (EBC). The assay is sample-to-answer all in a single step. Also, the assay is label-free and probe-free.

Use of reduced graphene oxide (rGO) electrode(s) allows for sensitive detection of nitrite. Advantageously, the electrodes are sensitive enough to quantify basal levels of nitrite in human samples. Gold electrodes and graphene oxide (not reduced) can be used, but are shown to have less sensitivity when compared to electrodes including rGO.

Use of square wave voltammetry (SWV) or differential pulse voltammetry (DPV) to measure nitrite concentration results in enhanced sensitive when compared to amperometry and cyclic voltammetry. (See, e.g., FIGS. 7 a-7d, 11A-11C, and 12A-12C, and associated description). The conditions required to operate DPV (including pulse width, frequency, and height) can be controlled to make the assay perform effectively.

Measurement of nitrite concentration in EBC using, for example, SWV is presented in a poster by A Gholizadeh, et al., entitled "Measurement of nitrite levels in exhaled breath condensate samples using electrochemically reduced graphene oxide based sensor," Jun. 5, 2016, the entire teachings of which are incorporated herein by reference. The poster outlines and illustrates the electrochemical process underlying the nitrite assay, manufacturing of a sensor device to perform the assay, and operation of the sensor device according to embodiments of the invention. Use of SWV to measure nitrite concentration is described in an article by Azam Gholizadeh, et al., "Toward point-of-care management of chronic respiratory conditions: Electrochemical sensing of nitrite content in exhaled breath condensate using reduced graphene oxide," Microsystems & Nanoengineering (2017) 3, 17022; doi:10.1038/micronano.2017.22; Published online: 22 May 2017, the entire teachings of which are incorporated herein by reference. The article further describes and illustrates (see, e.g., FIG. 7 and associated description) the electrochemical process underlying the nitrite assay, manufacturing of the sensor device to perform the assay, and operation of the sensor device and results obtained according to embodiments of the invention.

Nitrite in EBC is a more sensitive biomarker as compared to exhaled NO. Exhaled NO is a fleeting transient molecule, which is unstable and oxidizes to nitrite rapidly. For at least this reason, nitrite in EBC is a more stable state than exhaled NO.

Described herein is fabrication of a micro-electrochemical cell system that differs from prior approaches for assaying EBC, in that it allows for assaying small volumes of EBC (e.g., 100 µl or <30 µl), which is advantageous because it is generally difficult to obtain large volumes of EBC.

Also described herein is a useful coating method (modified drop-cast method), which can be used to coat gold (or other suitable electrode material) with a layer of rGO. In a preferred embodiment, the GO is electrochemically reduced, which allows for more reduction (see, e.g., Raman spectrum peak ratios in FIG. 3 of the article by Azam Gholizadeh, et al., Microsystems & Nanoengineering (2017) 3, 17022), as compared to thermal reduction and chemical reduction.

The devices and methods described here can directly detect and quantify biomarker(s) in EBC samples (e.g., EBC samples obtained from human subjects) without any sample pretreatment. This is in contrast to standard chemiluminescent methods, which require sample pretreatment.

The assay disclosed herein can be performed using SWV or DPV without the need for any enzyme or catalyzing particles like platinum. This is an unexpected and useful feature. Contrary to chemiluminescent assays, where there are many interfering molecules that must be chelated or neutralized, in the present electrochemical assay, at about 0.7V redox potential, only peaks in the current measured resulting from the presence of nitrite in EBC are observed; no other molecules appeared in the current measured.

Another unexpected result is that purging of oxygen is not necessary for the assay described herein. Most electrochemical assays require oxygen purging to get the processes to work, but the present assay does not. Thanks to the electrochemical properties of rGO, nitrite can be detected in a lower voltage range, sufficiently far away from the $H_2O$ interference peak, which makes it possible to conduct the assay without purging oxygen. This makes a portable assay feasible, e.g., a portable device to conduct the assay described herein. If oxygen purging was required, a portable device would be difficult, if not impossible, to implement due to the requirement of having an oxygen source to supply the oxygen for purging.

Potential applications of embodiments of the invention include a point of care (POC) diagnostic kit for asthma and other inflammatory conditions of the respiratory tract.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 2a-e illustrate a fabrication process for the reduced graphene oxide biosensor formed in a micro-electrochemical fluidic cell according to an example embodiment of the invention. FIG. 2a shows electrodes, e.g., screen printed electrodes (SPEs), and FIG. 2b shows dropping 2 micro-liter graphene oxide solution on top of a gold working electrode, creating a thin graphene oxide layer. FIG. 2c illustrates using a glass slide to create a smooth layer of GO, and FIG. 2d shows how a small volume area of the sensor sample well can be obtained with a PDMS membrane. FIG. 2e shows an image of a sensor useful for detection of nitrite.

FIGS. 9A-9C are scanning electron microscope (SEM) images of graphene oxide on Carbon electrode in different magnifications.

FIGS. 9D-9F are graphs of Raman spectroscopy data of Carbon working electrode (plot in FIG. 9D), GO thin film (plot in FIG. 9E) and rGO thin film (plot in FIG. 9F) on top of carbon electrode.

In FIG. 11B, data points and a linear curve fit are plotted for concentrations in the range 0 to 20 μM. In FIG. 11C, data points and a liner curve fit are plotted for concentrations in the range of 0 to 10 μM.

In FIG. 12B, data points and a linear curve fit are plotted for concentrations in the range 0 to 20 μM. In FIG. 12C, data points and a liner curve fit are plotted for concentrations in the range of 0 to 6 μM.

DETAILED DESCRIPTION

Figure 1:
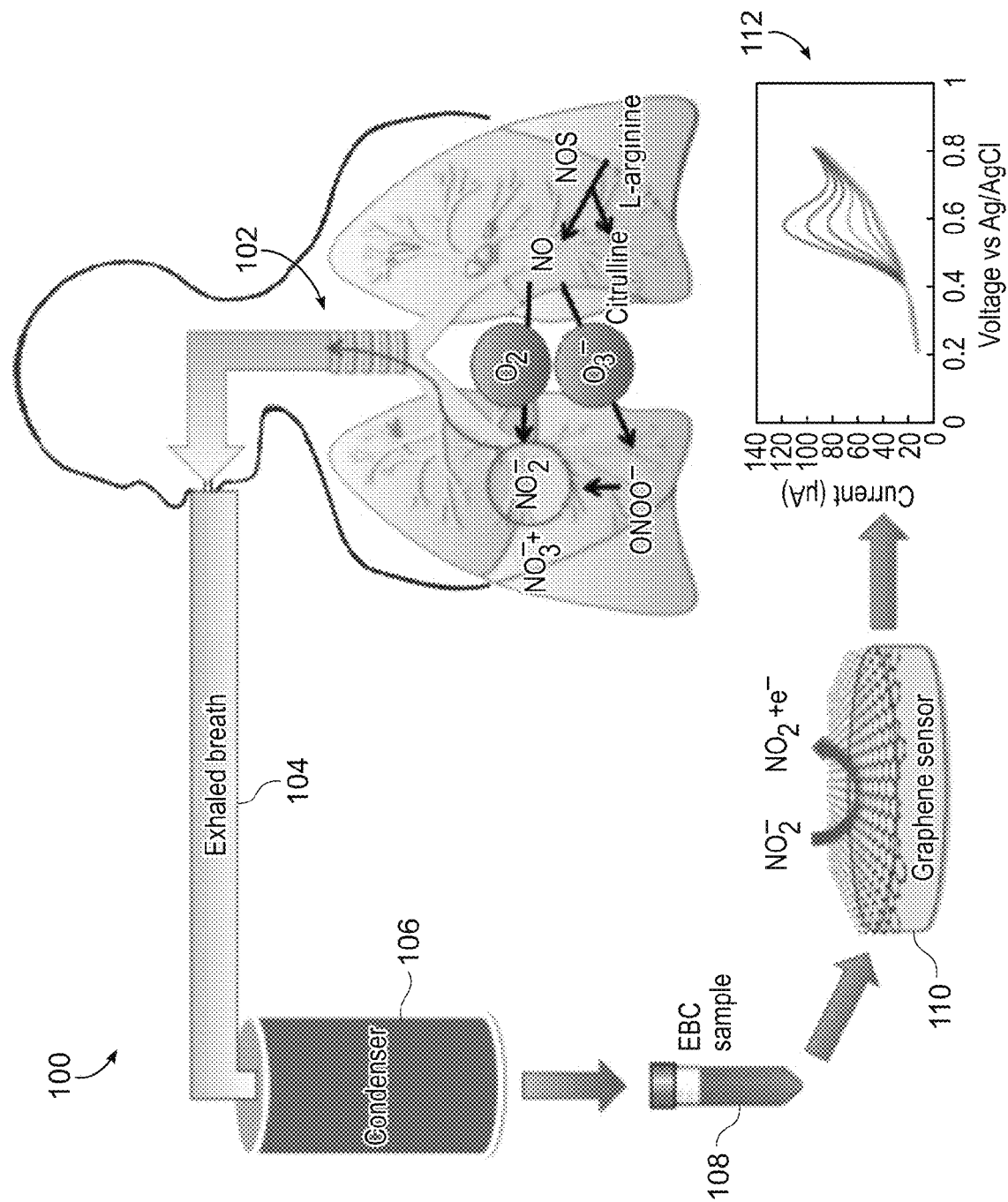
FIG. 1 illustrate an embodiment of a sensor device and method for measuring nitrite in an exhaled breath condensate (EBC) sample using reduced graphene oxide (rGO).

A description of example embodiments follows.

Measurement of biomarkers in exhaled breath condensate (EBC) can contribute to the molecular phenotyping of asthma, thus enabling targeted treatment and more effective disease management.

Current solutions for asthma diagnosis include personal and medical history, physical examination (e.g., x-ray, etc.), and lung function tests. Lung function tests can include:
a) Spirometry—recommended test to assess lung function by measuring inhale and exhale volume, often used to diagnose asthma, chronic pulmonary disease (COPD);
b) Peak airflow—handheld device for measuring the rate at which the patient can force air out of his/her lungs; and
c) Challenge tests—expose to known asthma triggers to induce a mild reaction.

Measurement of exhaled nitric oxide (NO) is used to assess disease. High levels of nitric oxide are associated with inflammation in the air way which could be indicative of asthma.

Measurement of exhaled breath condensate (EBC) is being investigated as a noninvasive method for studying the composition/inflammation of the fluid lining the airway. There are a variety of laboratory techniques to measure EBC. These techniques include pH measurement, gas chromatography/mass spectrometry and high-performance liquid chromatography. It is not known if EBC pH measurements provide accurate estimates of airway pH. Researchers have raised concerns regarding the standardization of EBC collection and measurement methods. (See, e.g., BlueCross BlueShield of Tennessee Medical Policy Manual.)

Nitrite is typically detected through spectrophotometric methods (Griess reaction) involving fluorimetry, chemiluminescence, or ion chromatography. In these methods, EBC samples need to be pretreated to induce the appropriate reaction and eliminate interfering compounds such as chlorine.

The use of biomarkers in EBC may help to overcome the difficulties associated with obtaining airway tissue and bronchoalveolar lavage samples that have significantly hampered the study of naturally occurring exacerbations of asthma. EBC contains droplets of airway lining fluid (ALF) that are exhaled during normal tidal breathing. In addition to condensed gas-phase compounds, EBC contains non-volatile compounds that originate from ALF, including hydrogen peroxide, nitrite and nitrate, as well as larger molecules such as eicosanoids, proteins, and even nucleic acids. The ability to non-invasively characterize airway tissue by repeated measurements of biomarkers in EBC can be useful for studying the time-course of dynamic inflammatory pathways that are involved in asthma exacerbation. Ultimately, EBC biomarkers may contribute to the assessment of different asthma phenotypes and the development of individualized rational approaches to asthma management at the point of care.

Exhaled breath condensate (EBC) generally comprises exhaled air passed through a condensing or cooling apparatus, resulting in an accumulation of fluid. Although EBC is primarily derived from water vapor, it also contains aerosol particles or respiratory fluid droplets, which in turn contain various nonvolatile inflammatory mediators, such as cytokines, leukotrienes, oxidants, antioxidants, and various other markers of oxidative stress. A variety of laboratory techniques are available to measure the components of EBC, including simple techniques such as pH measurement, as well as more sophisticated gas chromatography/mass spectrometry or high performance liquid chromatography, depending on the component of interest. (Source: Wellmark.com, Exhaled Nitric Oxide And Exhaled Breath Condensate, available online at https://www.wellmark.com/Provider/MedpoliciesAndAuthorizations/MedicalPolicies/policies/Exhaled_Nitric_Oxide.aspx, accessed Jun. 2, 2017)

Recent studies have shown the promise of EBC nitrite for use as a biomarker of both oxidative stress and inflammation in asthma. As illustrated in FIG. 1, the primary source of nitrite in the respiratory tract 102 of a human or animal is nitric oxide (NO), which is produced from L-arginine by nitric oxide synthase. In aqueous solution, NO reacts rapidly with reactive oxygen species (ROS) to form more stable nitrogen oxides, such as nitrite ($NO_2^-$) and nitrate ($NO_3^-$). Increased levels of NO are associated with inflammatory disease states such as asthma, COPD, and cystic fibrosis.

FIG. 1 illustrates an embodiment of a sensor device and method 100 for measuring nitrite in an exhaled breath condensate (EBC) sample using reduced graphene oxide (rGO). As shown, an EBC sample 108 is collected from exhaled breath 104 using a condenser 106 and nitrite content is measured electrochemically (112) using the sensor device 110.

Example method for sensor fabrication and characterization

Graphene oxide was prepared using the Hummers method. Screen-printed three-electrode micro-chips consisting of Ag/AgCl reference electrodes, platinum counter electrodes, and 5-mm gold working electrodes were commercially obtained (Metrohm, Herisau, Switzerland). The morphology of the graphene oxide was characterized using field-emission scanning electron microscopy (SEM) (Zeiss Ieo Field emission SEM, Carl Zeiss, Inc., One Zeiss Drive, NY, USA) and atomic force microscopy (AFM) (Digital Instruments Nanoscope IV, Digital Instruments, NY, USA). The atomic force microscope was operated in tapping mode using standard cantilevers with a spring constant of 40 N $m^{-1}$ and a tip curvature of o10 nm. FT-Raman spectra (Horiba Johin-Yvon Micro Raman Spectrometer, 532 nm excitation laser, HORIBA, NY, USA) were recorded to characterize the reduction of the graphene oxide substrates. Electrochemical measurements (PSTAT Princeton Instruments, Trenton, N.J., USA) were performed under ambient conditions. All potentials were applied with respect to the Ag/AgCl reference electrode.

FIGS. 2a-e illustrate an example process to fabricate an integrated reduced graphene oxide electrode/micro-electrochemical cell. First, a 3-μL aliquot of graphene oxide suspension ("GO drop" 205), which is synthesized from graphite powders using the Hummers method, is placed on the surface of a gold working electrode 202, as illustrated in FIGS. 2a and 2b. In addition to the gold working electrode 202 (shown as central "Au" electrode in FIGS. 2a-d), the electrode system includes a reference electrode 204 (shown as "Ag" electrode in FIGS. 2a-d) and a counter electrode 206 (shown as lateral "Au" electrode in FIGS. 2a-d). Next, a thin glass slide 212 is placed on top of the droplet to cast the GO onto the gold electrode forming a GO thin layer, as illustrated in FIG. 2c. Superfluous solution is aspirated, and the surface is dried at room temperature. The GO layer is then reduced electrochemically in acetate buffer (pH 5.5) using cyclic voltammetry between −1.6 and 0 V at a scan rate of 25 mV for 30 cycles under continuous $N_2$ purging. The micro-electrochemical cell is fabricated by forming a thin layer of PDMS on top of the insulated layers of the screen-printed electrode (SPE) micro-chip. Then, as illustrated in FIG. 2d, a thicker PDMS layer 214 containing an 8-mm hole is covalently bonded to the thin PDMS layer using $O_2$ plasma treatment. During $O_2$ plasma treatment, the rGO layer and the wire-bonding pads of the SPE micro-chip are protected with a glass slide. FIG. 2e illustrates the completed sensor 210.

Figure 3A:
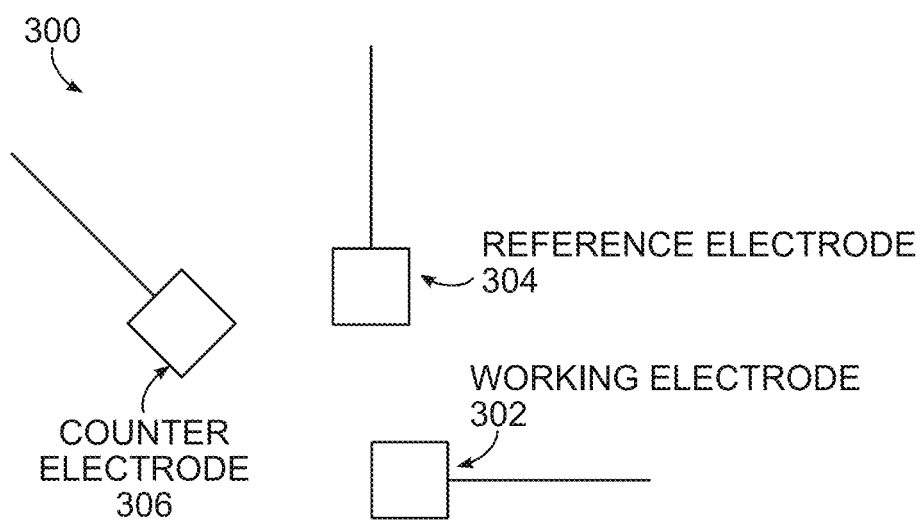
FIG. 3A schematically illustrates an example electrode arrangement for use with embodiments of the invention.

FIG. 3A illustrates an example electrode system 300 having a three-electrode configuration that includes a working electrode 302, a reference electrode 304, and a counter electrode 306. The working electrode 302 is used to measure the redux current. The reference electrode 304 is used to set the potential. The counter electrode 306 is used to inject sufficient current to ensure that the reference voltage is constant.

Figure 3B:
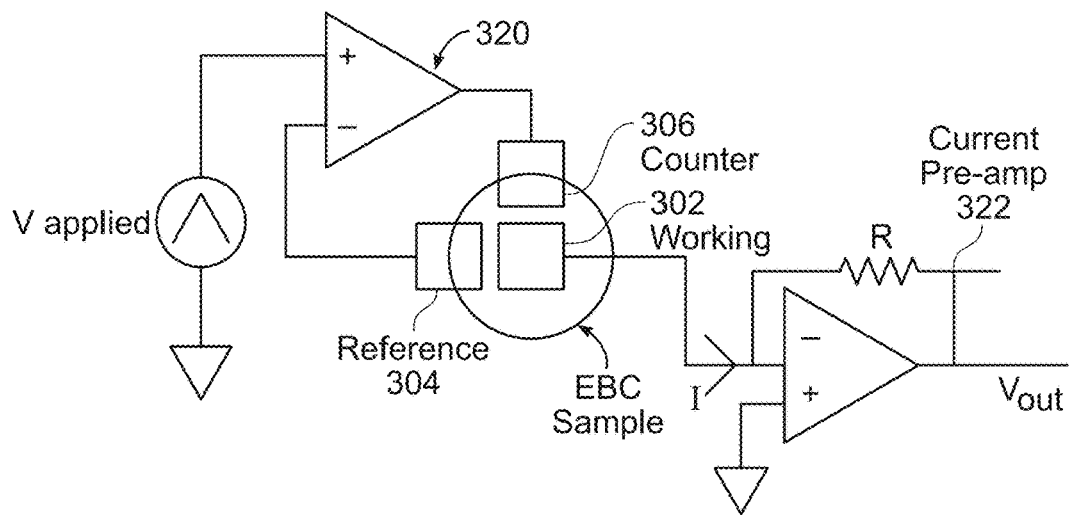
FIG. 3B illustrates example circuitry coupled to an electrode system (three electrode arrangement) for use with embodiments of the invention.

FIG. 3B illustrates example circuitry coupled to an electrode system (three electrode arrangement) for use with embodiments of the invention. A voltage (potential) $V_{applied}$ is applied to an EBC sample via a counter electrode 306 and a reference electrode 304 connected to an amplifier 320. A working electrode 302 is connected to another amplifier, current pre-amp 322, and a resistor R. By measuring the voltage $V_{out}$ the redox current I can be determined as $I=V_{out}/R$. Other means of measuring the redox current may be employed.

Figure 3C:
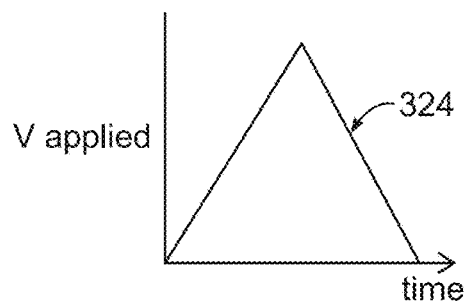
FIG. 3C illustrates an example voltage versus time curve that can be used with the electrodes and circuitry of FIG. 3B for conducting cyclic voltammetry.

FIG. 3C illustrates an example voltage versus time curve that can be used with the electrodes and circuit of FIG. 3B for conducting cyclic voltammetry. The figure illustrates one cycle of a cyclic voltage pattern. As shown, the voltage rises and falls in a triangular wave pattern 324, but other time-varying patterns, such as square-wave patterns can be used. The change in voltage over time can be characterized by specifying a scan rate.

Figure 3D:
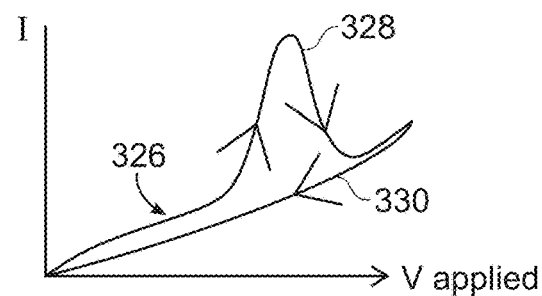
FIG. 3D illustrates a graph of current versus voltage representing example results obtainable using cyclic voltammetry.

FIG. 3D illustrates a graph of current (I) versus voltage ($V_{applied}$) representing example results obtainable using cycle voltammetry. Arrows on the current versus voltage curve 326 indicate the direction of rise in voltage followed by decline in voltage, following an applied voltage pattern such as shown in FIG. 3C. As can be seen, the current versus voltage curve exhibits a peak 328 on the rising phase and shows hysteresis 330 on the declining phase.

Figure 3E:
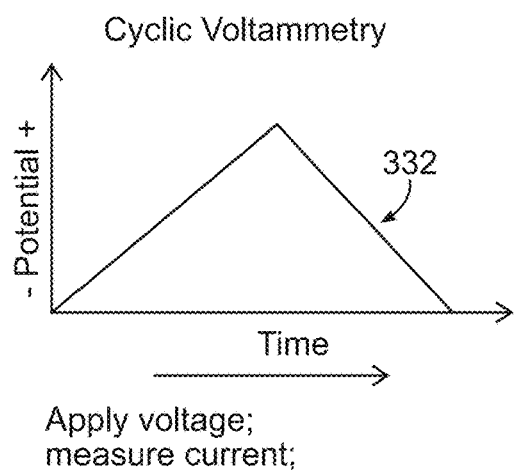
FIG. 3E is a schematic diagram illustrating another example voltage pattern for use in cyclic voltammetry.

FIG. 3E is a schematic diagram illustrating a voltage pattern for cyclic voltammetry. The time-varying voltage pattern 332 is applied to a sample and a resulting current is measured. As shown in FIG. 3E, the voltage (e.g., potential) rises linearly from a base value to a peak value and then falls back to the base value exhibiting in a triangular wave pattern. This is one suitable voltage pattern for cyclic voltammetry, but other voltage patterns can be used. Scan rate is the change in applied voltage over time (e.g., slope) and can be specified in millivolts per second (mV/s). The scan rate can be adjusted to suit the conditions of the voltammetry process. Example scan rates are in the range of 25-50 mV/s, but other scan rates can be used.

FIGS. 4a-d show graphs illustrating example current versus voltage curves obtained by cyclic voltammetry using rGO and GO electrodes of example embodiments under various experimental conditions.

Figure 4A:
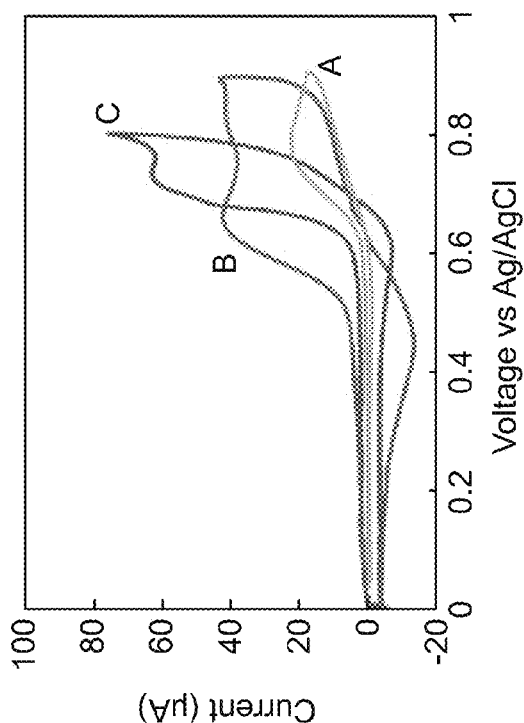
FIG. 4a is a graph illustrating current versus voltage curves obtained using cyclic voltammetry and the rGO electrode. The curves (A through D) represent results for: (A) PBS after washing three times; (B) 5 mM nitrite in acetate buffer, pH 6, (C) 0.1 M KCl, and (D) PBS buffer, pH 7.4.

After fully reducing the GO electrode, the electrochemical performance of the platform for nitrite detection was characterized. Because both electrolyte identity and pH affect the sensitivity and detection limit of the sensor, the electrochemical response of the rGO sensor was investigated using cyclic voltammetry in various electrolytes. FIG. 4a shows the oxidation peak of 5 mM nitrite in phosphate-buffered saline (PBS, pH 7.4), 0.1 M KCl, and acetate buffer (pH 6) as measured at a scan rate of 50 mV/s. Anodic peaks appeared at 0.69, 0.7, and 0.63 V for the PBS, KCl, and acetate buffers, respectively. Given that a goal of this work is to develop a portable sensing platform that can operate under ambient conditions (in which $O_2$ may react with the analyte), the present approach avoided purging $O_2$ in the samples. This enabled assessing how the sensor performs on biological samples under ambient conditions.

As seen from the voltammetry measurements conducted in EBC samples, the voltage of the oxidation peaks is shifted to positive voltages; this is more a favorable regime to use due to the lower over-potentials. Therefore, acetate buffer (pH 6) is the electrolyte chosen for the remainder of the experiments. Another important factor in deciding to use acetate is the fact that EBC samples from patients with inflammatory disease are reportedly acidic. Thus, pH 6 more closely approximates the actual pH of EBC samples obtained from patients with chronic inflammatory disease.

Figure 4B:
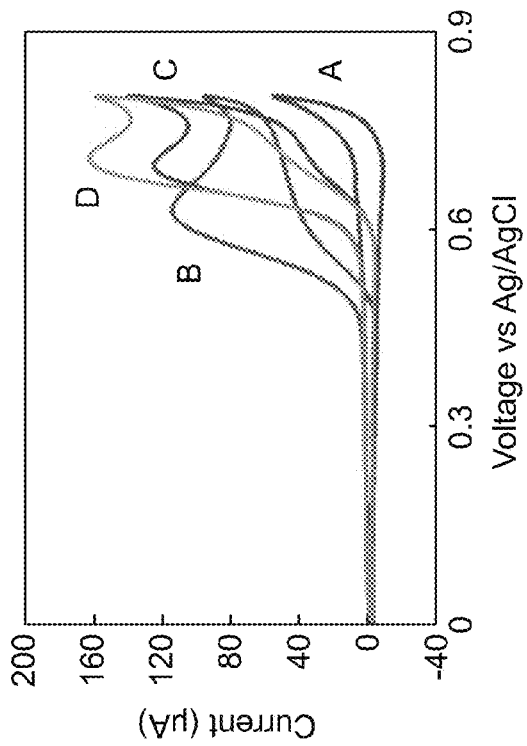
FIG. 4b illustrates data for cyclic voltammetry measurements of 1 mM nitrite and (A) the gold electrode of SPE and rGO in (B) acetate buffer, pH 6, and (C) PBS buffer, pH 7.4, respectively. The voltage range is 0-0.9 V, and the scan rate is 50 mV/s.
Figure 4C:
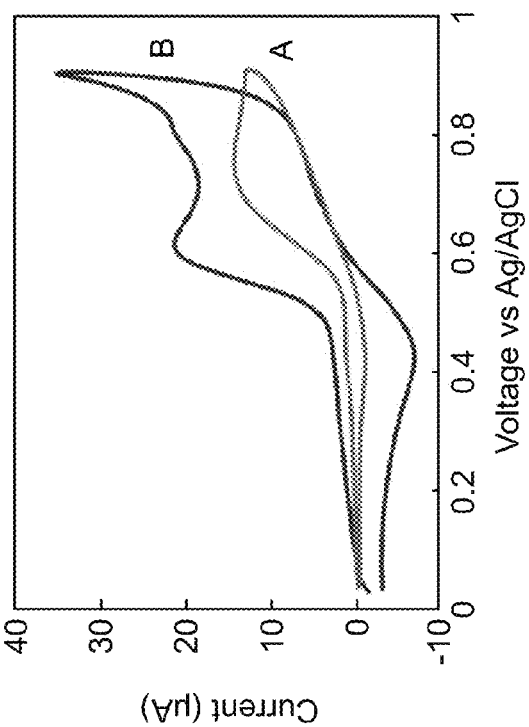
FIGS. 4c-4d illustrate cyclic voltammetry of (A) GO, (B) rGO in the presence of 100 μM and 1 mM nitrite. The scan rate is 25 mV/s.
Figure 4D:
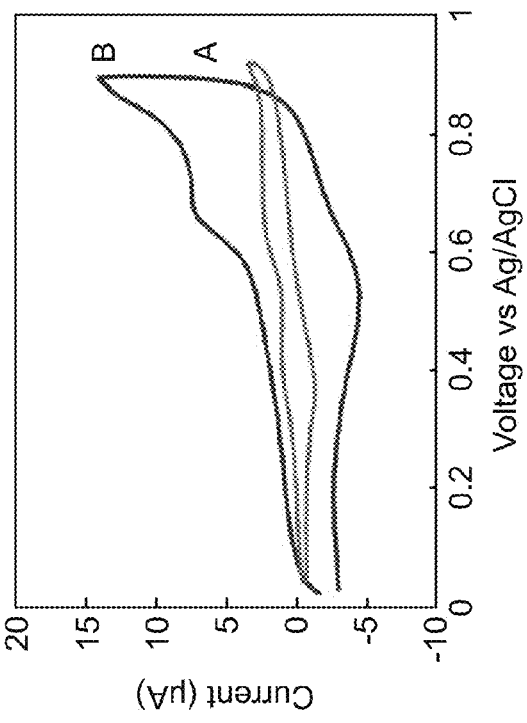

The performance of the rGO-modified electrodes was compared to those of the SPE- and GO-deposited electrodes. FIG. 4b shows a comparison between the anodic peaks in the presence of 1 mM nitrite for rGO electrodes at pH 6 (curve B) and pH 7.4 (curve C) and those for the SPE electrodes at pH 6 (curve A) (50 mV/s scan rate). As clearly seen from the figure, rGO has a higher current and lower over-potential than the unmodified SPE electrode. FIGS. 4c and 4d also show the response of both the GO-modified (curve A) and rGO-modified (curve B) electrodes in the presence of 100-1000 μM nitrite, respectively (scan rate, 25 mV/s).

Figure 5A:
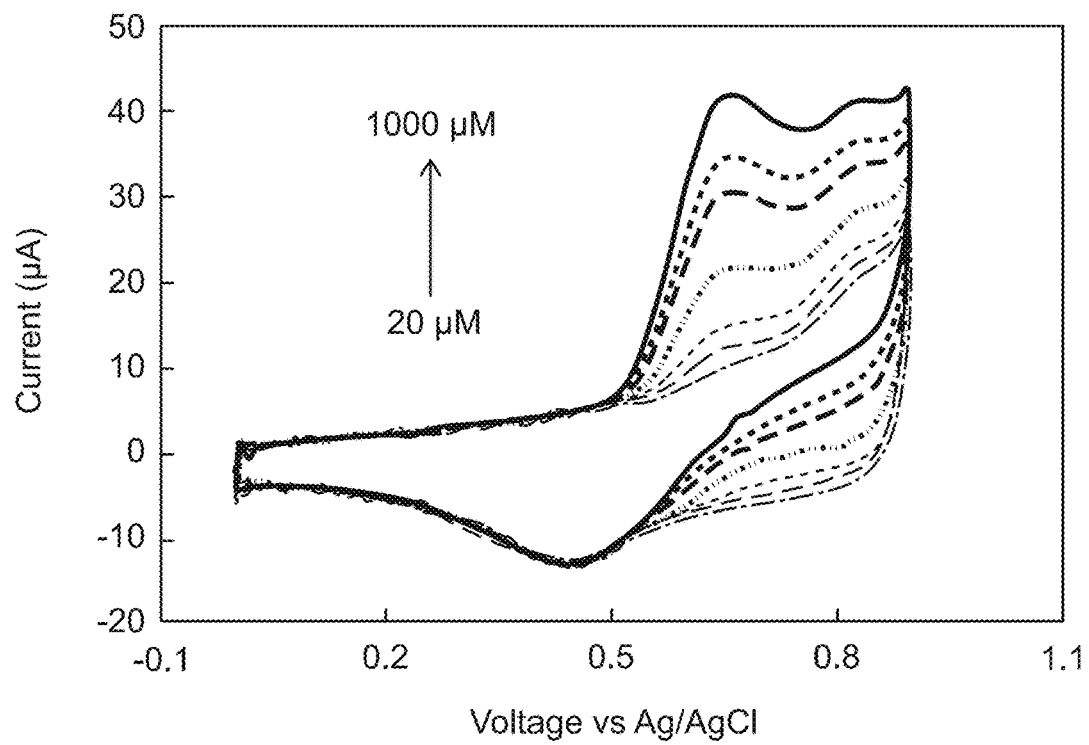
FIG. 5 illustrates example current versus voltage curves obtained using (a) cyclic voltammetry of varying concentrations of nitrite from 20 to 1000 μM at pH 6 with a scan rate of 50 mV/s; and (b) square wave voltammetry of varying concentrations of nitrite. Square wave voltammetry was also performed from 0 to 0.9 V with a step potential of 10 mV, an amplitude of 50 mV, and a frequency of 5 Hz.
Figure 5B:
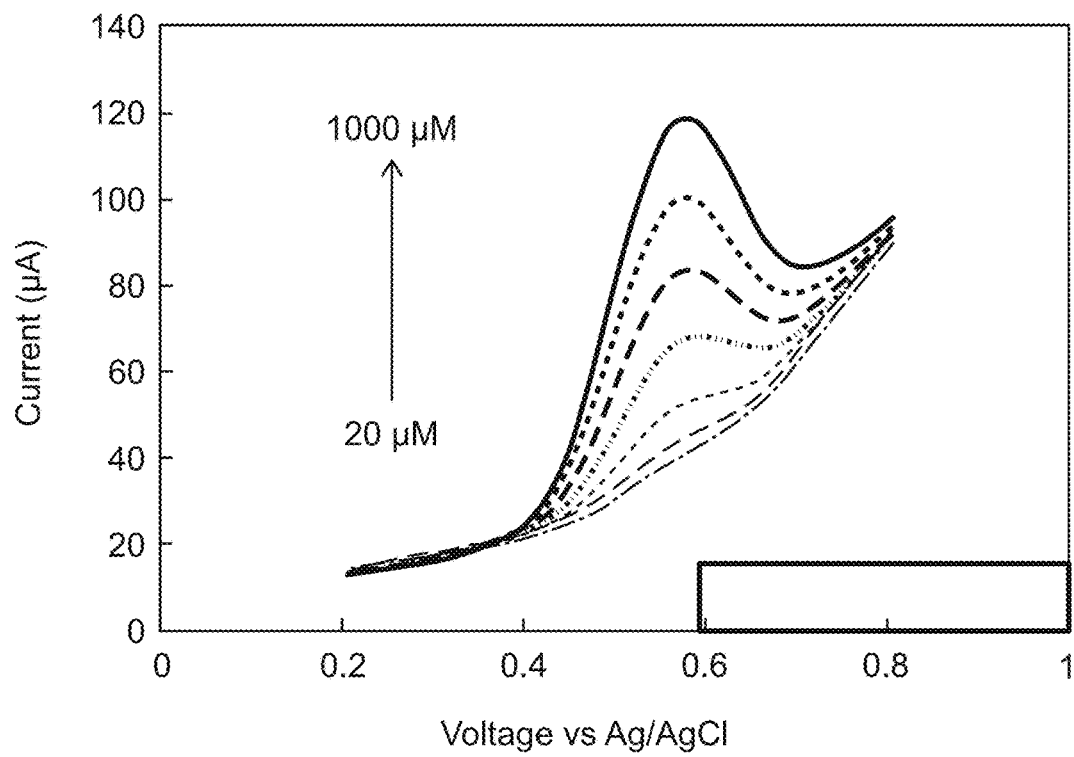

FIGS. 5a-b show the result of (a) cyclic voltammetry and (b) square wave voltammetry analysis for nitrite concentrations from 20 to 1000 μM (scan rate, 50 mV/s). The figures shown that using square wave voltammetry is useful to obtain relatively higher local peaks in current versus voltage curves, which can translate into more reliable estimates of nitrite concentration.

FIGS. 6a-d illustrate detection of nitrite in clinical EBC samples. After the performance of the fabricated sensor was confirmed in a standard electrolyte containing various concentrations of nitrite, the graphene-based sensors were tested in the complex biological matrix of EBC to study the effects of that biological matrix on the sensor. The results obtained provide insight into the response expected for clinical samples.

Figure 6A:
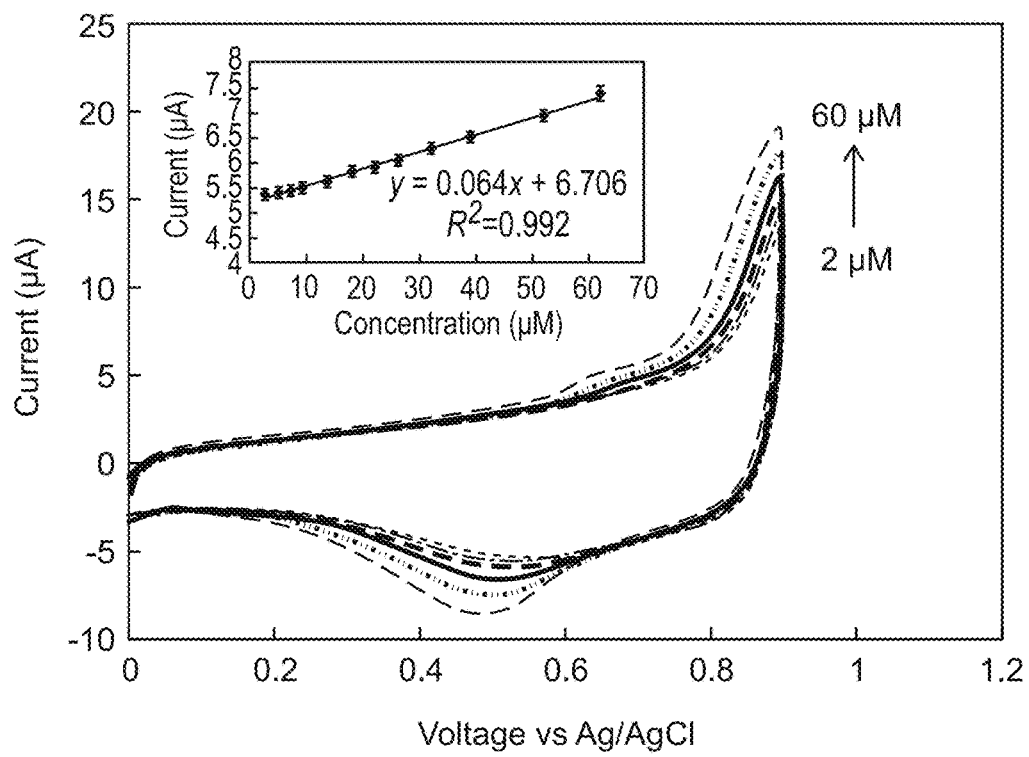
FIGS. 6a-b illustrate cyclic voltammogram data of rGO electrodes at different nitrite concentrations ranging from 2 to 60 μM and 100 to 900 μM, which were spiked into the EBC samples (scan rate of 25 mV/s).
Figure 6B:
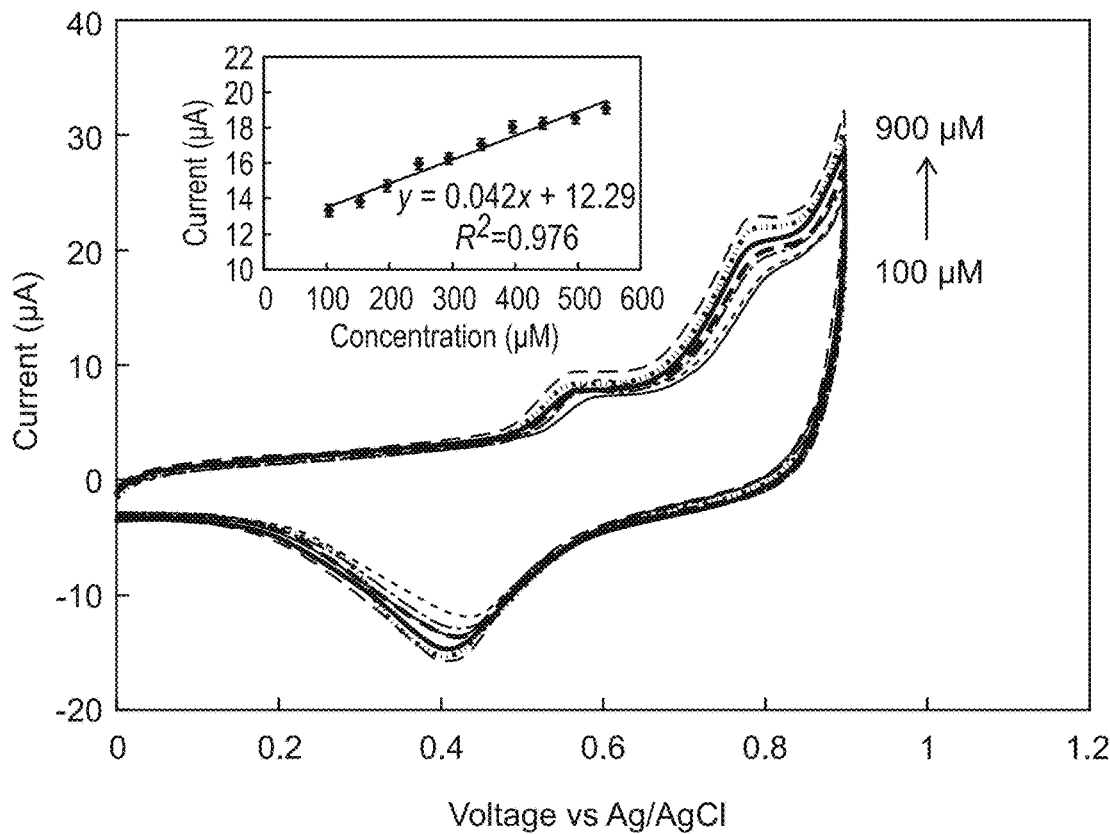
Figure 6C:
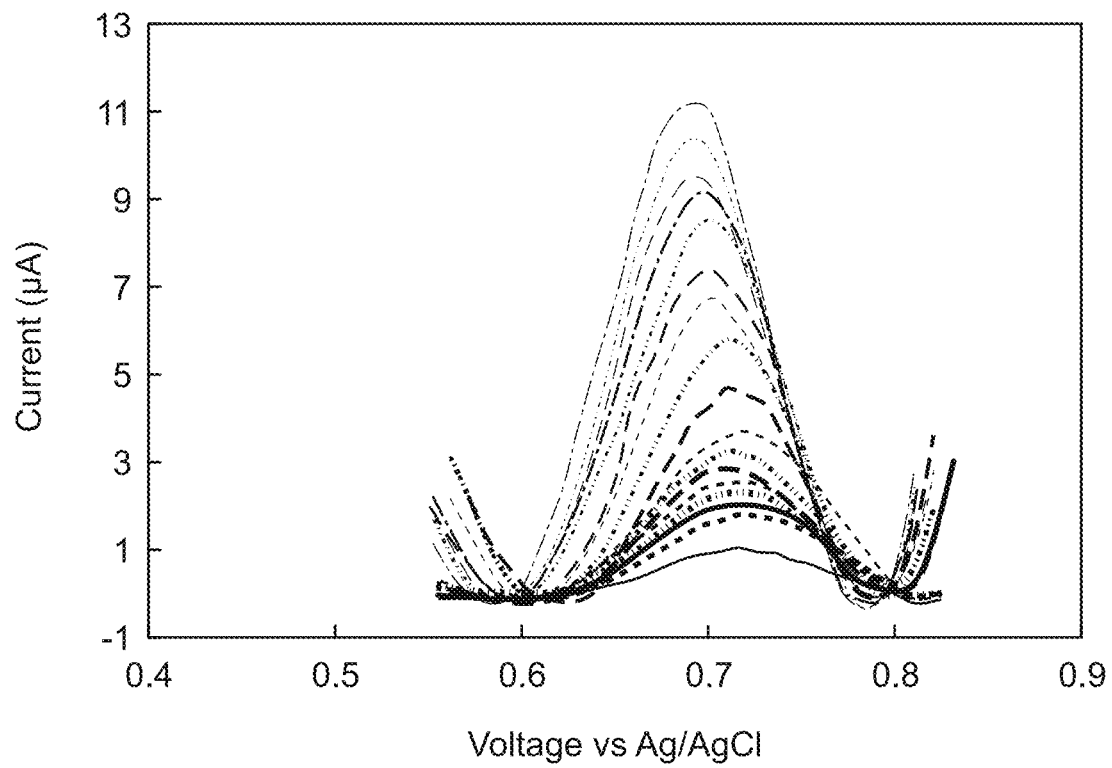
FIG. 6c illustrates square wave voltammogram data of spiked (concentration range from 0 to 1000 μM) EBC samples. The pulse amplitude is 50 mV.
Figure 6D:
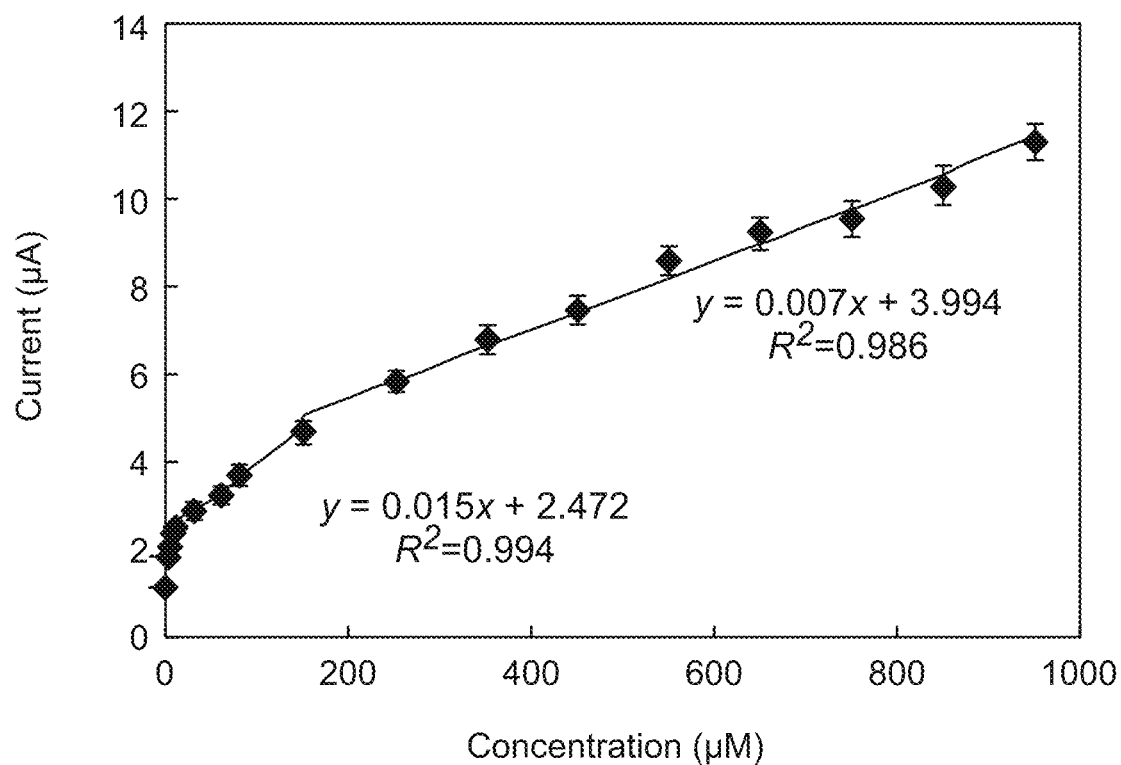
FIG. 6d illustrates an example calibration curve showing the respective slopes.

Nitrite levels in EBC have been reported in the μM range. Both cyclic voltammetry (CV) and square wave voltammetry (SWV) were used to measure the redox current resulting from spiking buffer solutions with various concentrations of nitrite into the EBC sample. FIGS. 6a and 6b show the voltammetric response of the sensor to solutions containing 2-1000 μM nitrite at a scan rate of 25 mV/s. The magnitude of the redox current generated for 1 mM nitrite was similar between the EBC and buffer solution matrices (FIG. 6d). However, as previously mentioned, the potential in the EBC was shifted to a higher over-potential of 0.79 V. This can occur because the presence of proteins in EBC samples can slow electron transfer. The insets shown in FIGS. 6a and 6b are calibration curves based on CV measurements. As shown, the current response is linear in the concentration range of interest.

The analytical performance of the nitrite sensor can be assessed by taking SWV measurements conducted in the range of 0-0.9 V. FIG. 6c displays the square wave voltammograms of nitrite in the range from 2 to 1000 μM. The redox current peak is found at 0.7 V. FIG. 6d shows the calibration curve obtained using SWV.

Figure 7A:
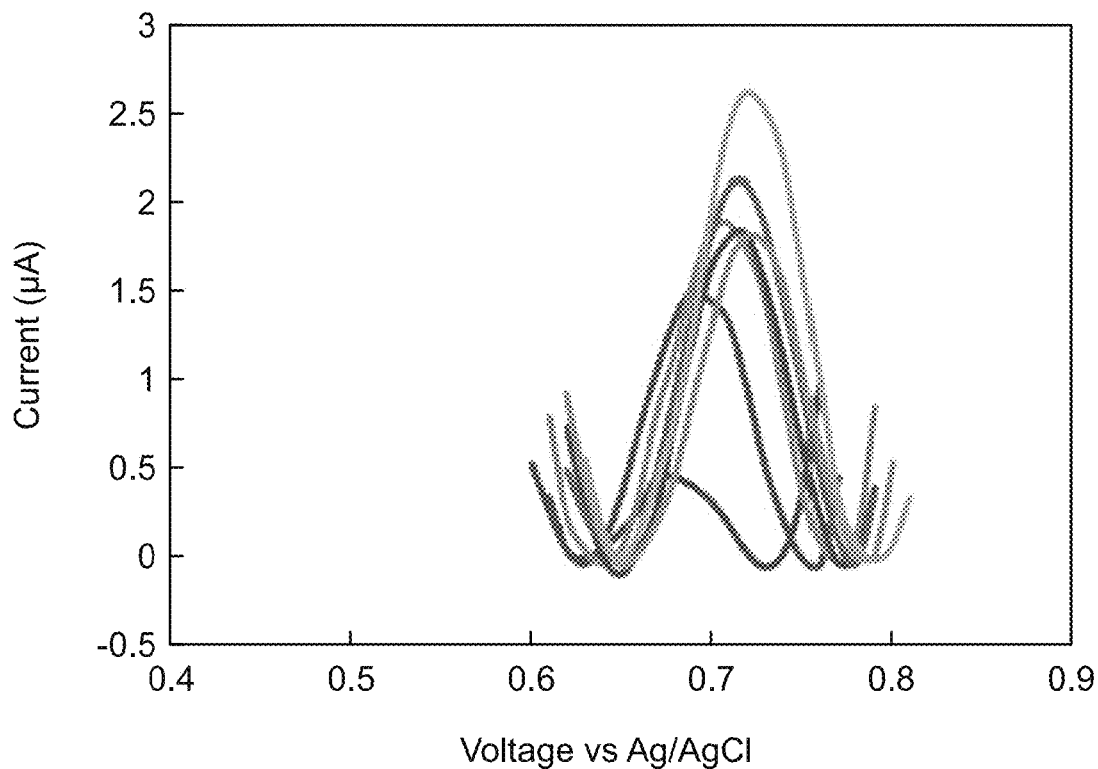
FIG. 7a illustrates square wave voltammogram data obtained for seven EBC samples.
Figure 7B:
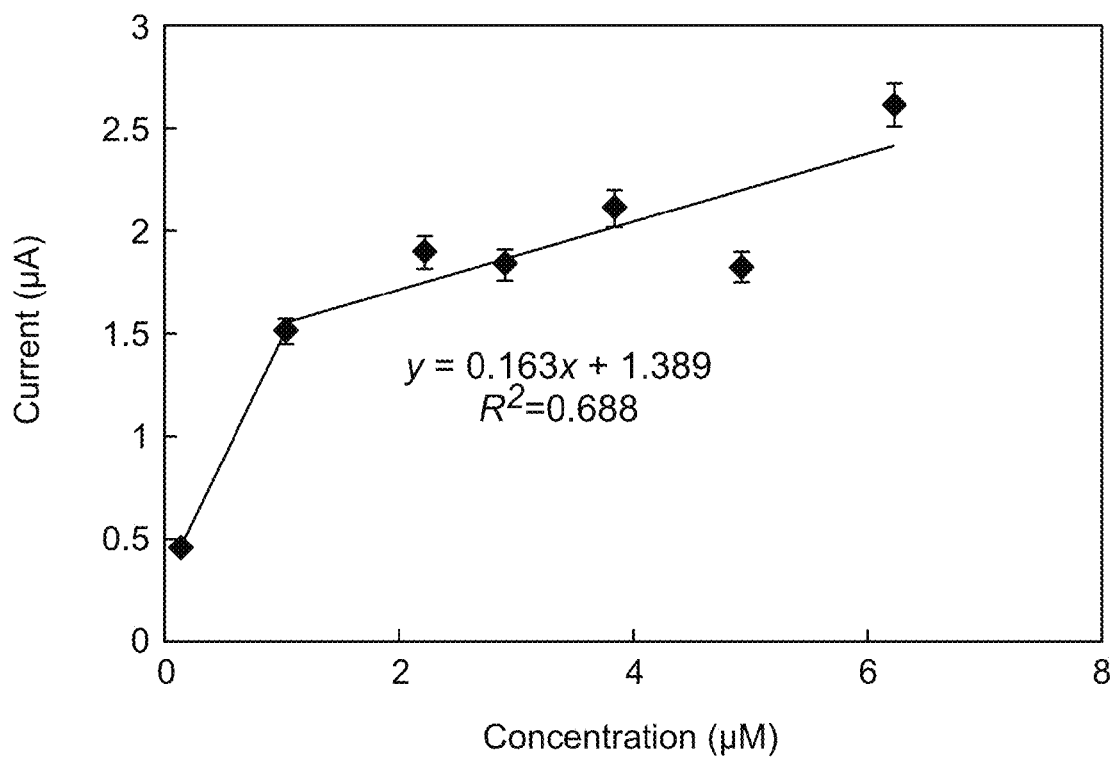
FIG. 7b illustrates the calibration curve obtained based on results obtained using spiked samples.
Figure 7C:
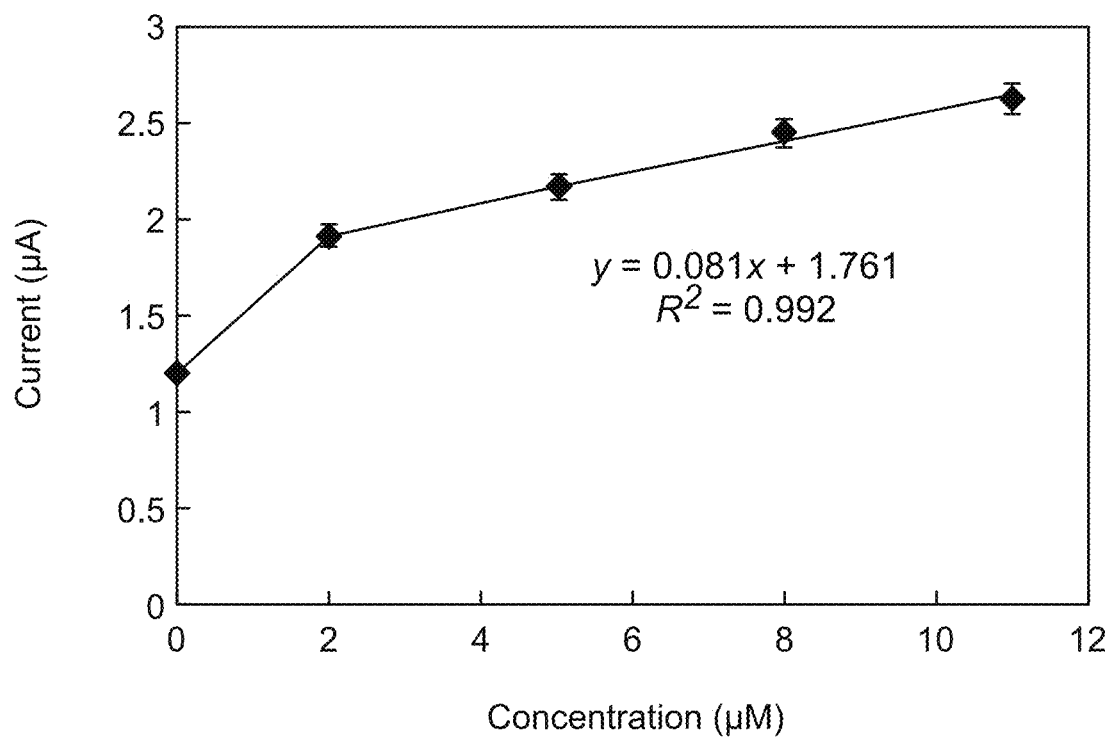
FIG. 7c illustrates a calibration curve based on chemiluminescence data.
Figure 7D:
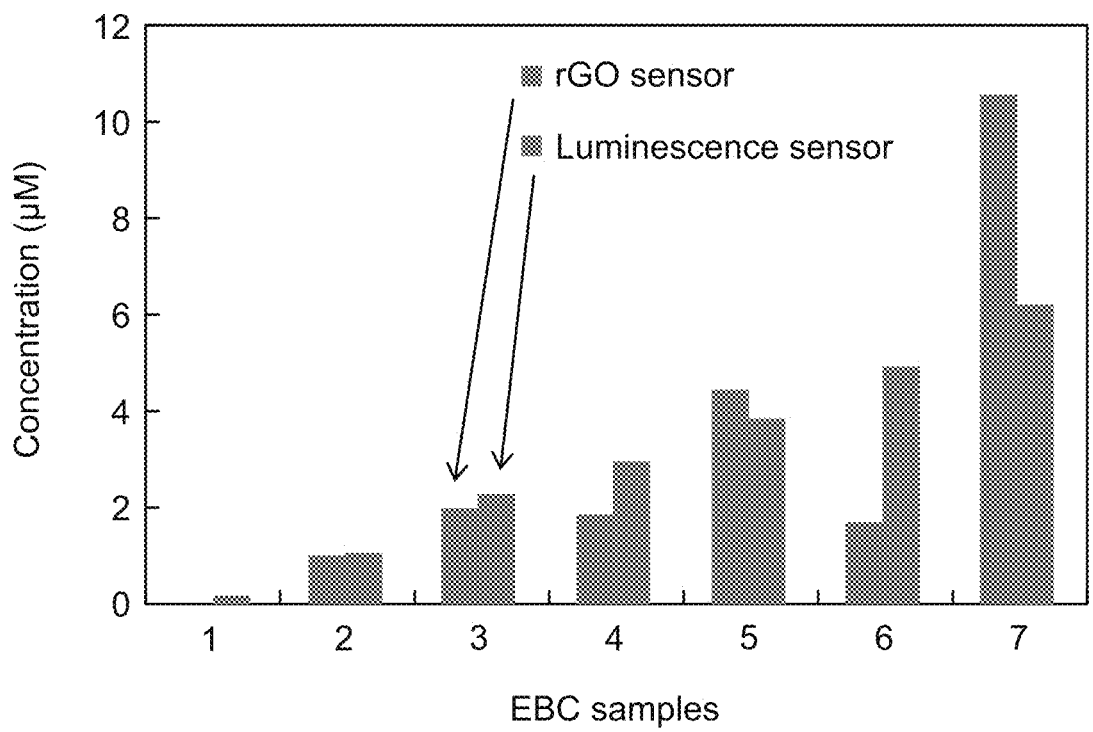
FIG. 7d shows comparison between predicted concentration and chemiluminescence data.

After validating the functionality of the rGO nitrite sensor with spiked EBC samples, accuracy of the devices was tested using a set of seven previously characterized clinical EBC samples. Square wave voltammetry (SWV) was performed for each of the seven characterized samples, as illustrated in FIG. 7a. The slight differences in oxidation potential between samples are believed to be due to differences in the complex EBC matrix between individuals. The nitrite concentration in each sample was calculated from the measured oxidation currents based on the calibration data obtained using the spiked standard nitrite solutions in EBC, the results of which are illustrated FIG. 7b. The accuracy of the measurements was benchmarked by comparing the readings from the graphene-based sensor with measurements obtained using an ozone-based chemiluminescence technique. FIGS. 7c and 7d show results of this comparison. The range of measured nitrite concentrations based on the chemiluminescence experiments is 0.14-6.5 μM. For at least five of the seven samples, the relationship is linear, and strong agreement is found between the results obtained using the rGO sensor and the chemiluminescence measurements.

Regarding the two outlying data points (samples 6 and 7, FIG. 7*d*), more experimentation may be necessary to understand the possible reasons behind their deviation. One possibility relates to the fact that the EBC samples were collected, frozen, and characterized by chemiluminescence several years prior to the electrochemical characterization experiments that were performed in this current study. This opens up the possibility that the nitrite content might have degraded over time in the frozen EBC samples (due to the possible conversion of nitrite to nitrate), thus highlighting the need for methods that can be used to measure samples at point-of-use immediately upon their collection from patients.

As illustrated in FIGS. 13A-13D, described below, there can be differences in measurement results when using fresh as compared to previously frozen EBC samples.

In this experiment, acetate buffer (pH 6) was added to the EBC samples in a 1:1 ratio, and it was assumed that the pH and conductivity of the samples were consistent between samples; however, it is possible that this assumption was not completely valid and that pH and conductivity might have varied between samples. Because the EBC sample volumes were small, it was not feasible to use a standardized pH meter electrode to measure pH; thus, it was not possible to independently validate the consistency of pH and conductivity among the samples. To correct this problem, the integration of a microfabricated pH sensor and conductivity sensor on the same sensor chip (e.g., coupled to the sample collection area) can provide insights that would allow more precise comparisons between samples.

Figure 8:
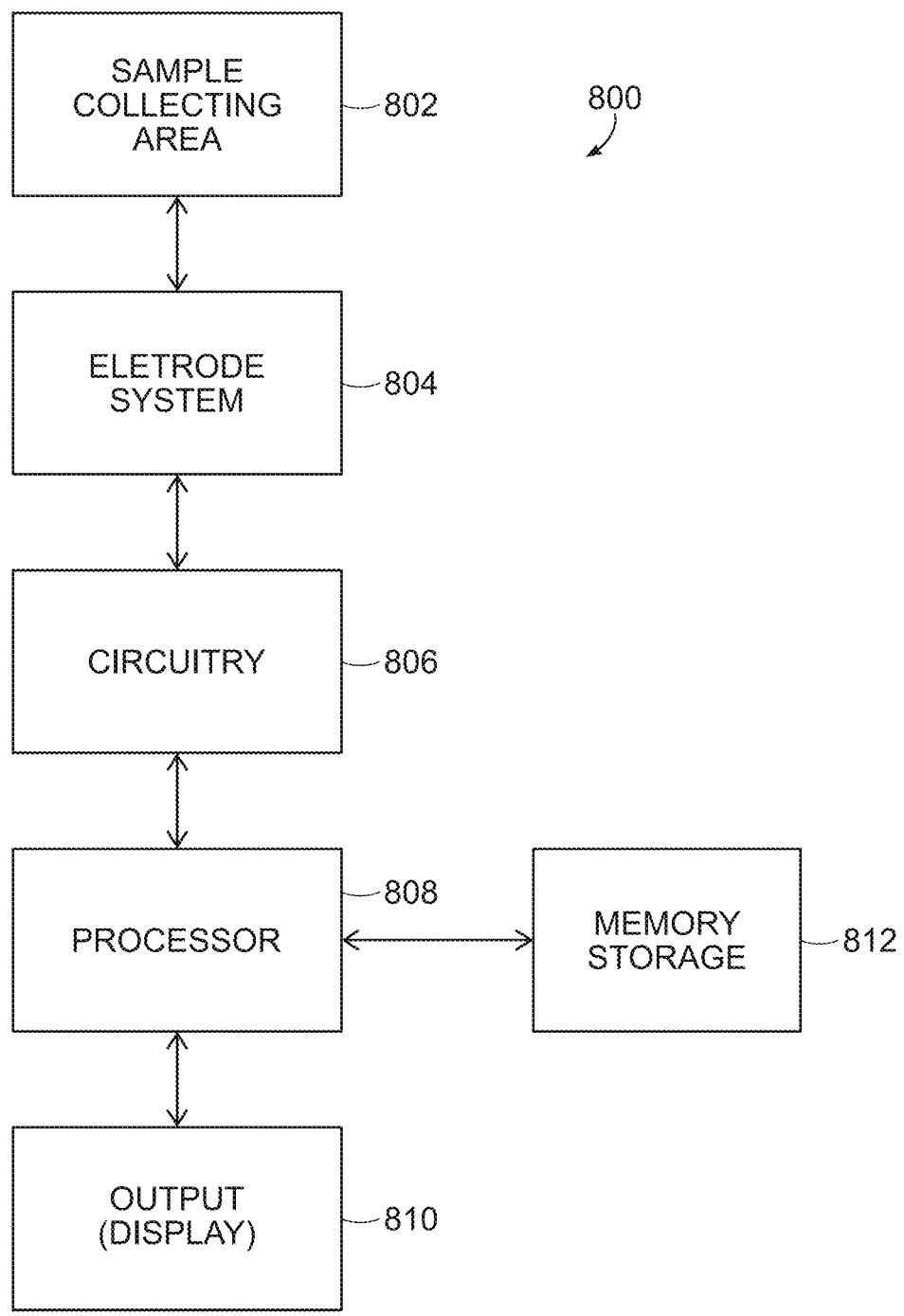
FIG. 8 is a block diagram of a device for detecting one or more biomarkers in exhaled breath condensate (EBC) according to an example embodiment of the invention.

FIG. 8 is a block diagram of a device and associated method for detecting one or more biomarkers in exhaled breath condensate (EBC) according to an example embodiment. The device includes a sample collection and/or holding area 802 to receive an exhaled breath condensate (EBC) sample obtained from a respiratory system, e.g., of a mammalian subject. An electrode system 804 is coupled to the sample collection area, the electrode system including reduced graphene oxide (rGO), e.g. on a working electrode. The device further includes circuitry 806 coupled to the electrode system 804, such as illustrated in FIGS. 3B-3D. The circuitry 806 is configured to apply a voltage to the EBC sample in the sample collection area via the electrode system and to measure a current via the electrode system in response to the voltage applied, in order to determine a concentration of nitrite in the EBC sample based on the current measured. The device can further include a processor 808 in communication with the circuitry 806 and with a memory storage 812, which may be integrated into the device or be remote memory storage. The processor 808 can communicate with an output device 810, such as a display unit. Communication with the processor 808 can be wireless, e.g., via Bluetooth or other wireless communication protocols. The processor can be configured to retrieve calibration data from the memory storage 812 and to calculate the concentration of nitrite based on the current measured and the calibration data retrieved from the memory storage. Responsive to the concentration of nitrite, an indication may be generated and displayed via output device 810. In an embodiment, the indication is that the subject is asthmatic at threshold concentration levels of the determined concentration of nitrite.

Chronoamperometry is an electrochemical technique in which the potential (voltage) of the working electrode is stepped and the resulting current from faradaic processes occurring at the electrode (caused by the potential step) is monitored as a function of time.

Graphs showing chronoamperometry results and other empirical data, in particular regarding use of calibration data and derivation of specific (optimized) redox voltage at which to assess peak current, are shown in Appendix C of U.S. Provisional Application No. 62/515,244, the entire teachings of which are incorporated herein by reference. Also shown in Appendix C of U.S. Provisional Application No. 62/515,244 are calibration curves and results of measurements that show that rGO has increased sensitivity over GO.

Additional empirical data regarding derivation of specific (optimized) redox voltages for assessing peak current in various EBC samples (e.g., collected using different methods/devices) and, in particular, regarding differences in measured parameters between fresh and frozen EBC samples, are presented in Appendix D of U.S. Provisional Application No. 62/515,244, the entire teachings of which are incorporated herein by reference, and in the following example.

EXAMPLE

Nanomolar Detection of Respiratory Inflammation Metabolites in Exhaled Breath Condensate Using Reduced Graphene Oxide Sensor: Study Effects of Sample Matrix and Storage Presented herein is a sensitive nitrite electrochemical sensor in exhaled breath condensate samples using reduced graphene oxide. Nitrite is one of the important biomarkers in respiratory system that can help monitoring lung inflammation diseases and lung cancer. In addition, we studied the effect of storage and important analytical parameters in electrochemical methods such as electrolyte type, EBC matrix effect and pH. These results can help to develop non-invasive, portable sensor for lung metabolite detection. Moreover, standardization of storage and analytical method can help to introduce this method for reproducible clinical applications

INTRODUCTION

Measuring biomarkers in exhaled breath condensate (EBC) can non-invasively monitor inflammation in the respiratory system. Among the many molecules detected in EBC, nitrite and nitrate are the stable end products of metabolism of nitric oxide. Increased amounts of these molecules have been found to be related to the level of inflammation in the respiratory systems (see M. Corradi, et al., Nitric Oxide, 8, 26 (2003)). Several methods, such as Griess reaction, photoluminescence, and mass spectroscopy, have been used to detect the quantity of nitrite in EBC samples (see W. Cao, et al., Crit. Rev. Anal. Chem, 37, 3 (2007)). These methods have high sensitivity; however, they require pretreatment and are not suitable for portable applications. Recently, an electrochemical graphene based sensor that can detect nitrite in EBC was reported (see A. Gholizadeh, et al., Microsystems & Nanoengineering, 3, 17022 (2017)). This sensor can be portable; however, it can benefit from further optimization to achieve detection in the nanomolar range. Moreover, standardization of new methods for clinical application is needed. Especially in EBC samples, the source of variation can be related to the technique of sample collection, processing, and analysis.

The aim of the presented work is two-fold. It seeks to improve the sensitivity of analysis and study stability of nitrite during storage. Moreover, as with electrical detection, the conductivity and nature of the matrix are very important; these parameters have been studied with variation of electrolytes and electrochemical impedance spectroscopy.

Experimental Methods

For monitoring these parameters, a reduced graphene oxide modified screen-printed electrode was used. Working electrodes were spin coated with graphene oxide and reduced electrochemically. Then, oxidative nitrite was detected with differential pulse voltammetry. The uniformity and reduction level of graphene oxide was studied using SEM and Raman spectroscopy. Also, the effect of the matrix has been studied in different electrolytes. Common devices to collect EBC from patients are the RTUBE™ breath condensate collection device by Respiratory Research Inc. (referred to herein as "R-tube") and the ECOSCREEN collection device by FILT—Lung- and Thorax Diagnostic GmbH (referred to herein as "EcoScreen"). EBC blanks obtained from R-tube and EcoScreen have been used as the basic matrix to have most similar electrolyte to EBC samples for comparison of results with standard electrolytes.

In addition, the case study of fresh real EBC samples has been performed. The sensor successfully distinguished between patients and blank samples with detection limit as low as nanomolar range without any pretreatment. Results show that the sensor can detect nitrite as low as 250 μM with high sensitivity. In addition, storage of the sample causes a decrease in the amount of nitrite, likely due to freezing. This study demonstrates the improvement in accuracy obtained from real-time measurement of nitrite in EBC.

Results:

FIGS. 9A-9F show SEM and Raman analysis of reduced graphene oxide. The SEM images in FIGS. 9A-9C show representative data obtained from a larger area of the GO layer that was directly deposited on a carbon electrode. These images show that the fabrication process (see, e.g., FIGS. 2a-2e and associated description) can fully cover the surface uniformly, even on a carbon-working electrode with a surface roughness of several microns.

Raman data presented in FIGS. 9D-9F show the spectrum of the GO substrate before reduction, and for the same substrate after 30 cycles of electrochemical reduction. The data shown represent the average of three measurements that were recorded at different areas/spots on each sample.

Figure 10A:
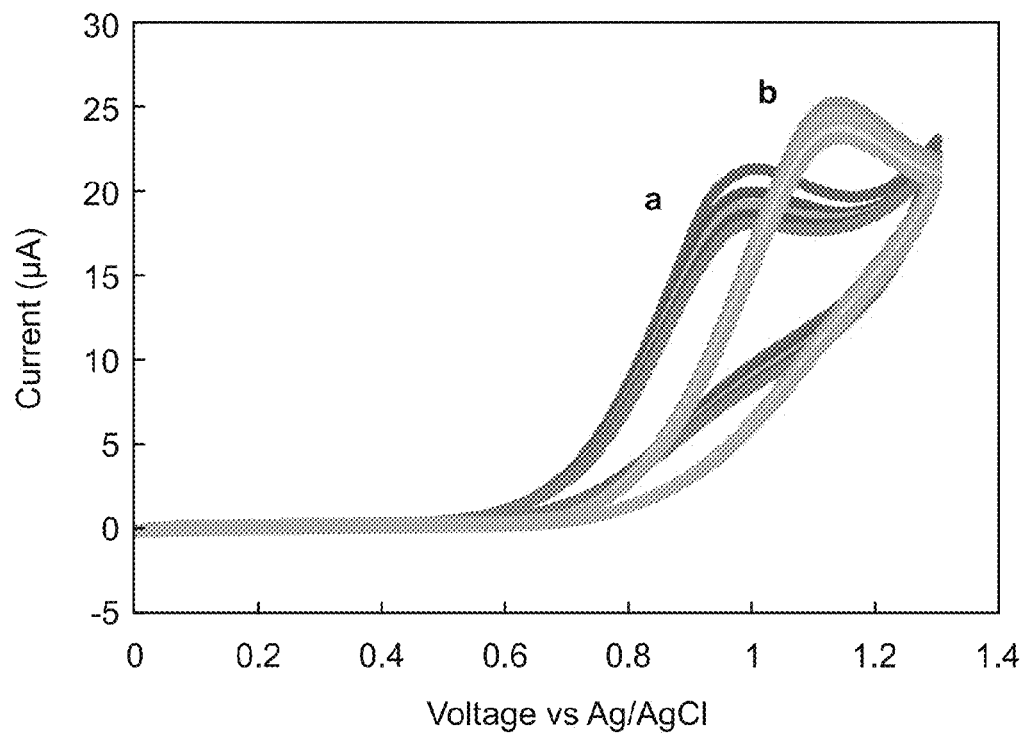
FIG. 10A illustrated Cyclic Voltammetry (CV) of 1 mM nitrite in acetate (curves a) and in PBS solution (curves b).
Figure 10B:
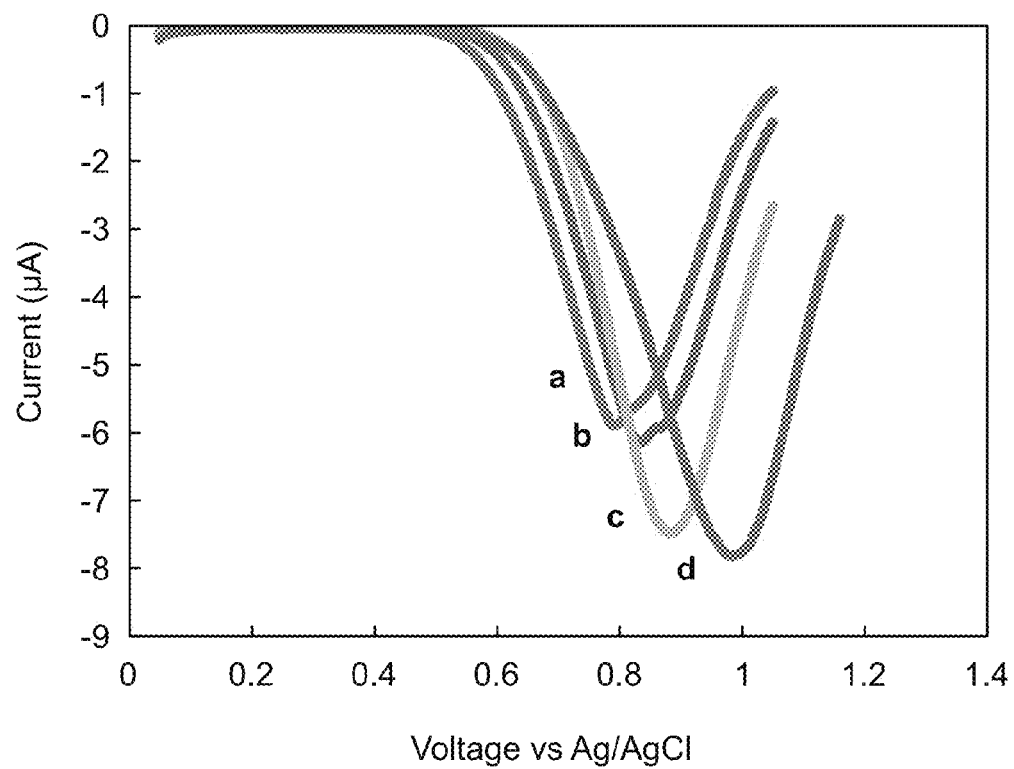
FIG. 10B illustrates differential pulse voltammetry (DPV) in (a) R-tube bulk, (b) Eco-screen bulk, (c) acetate, and (d) PBS.
Figure 11A:
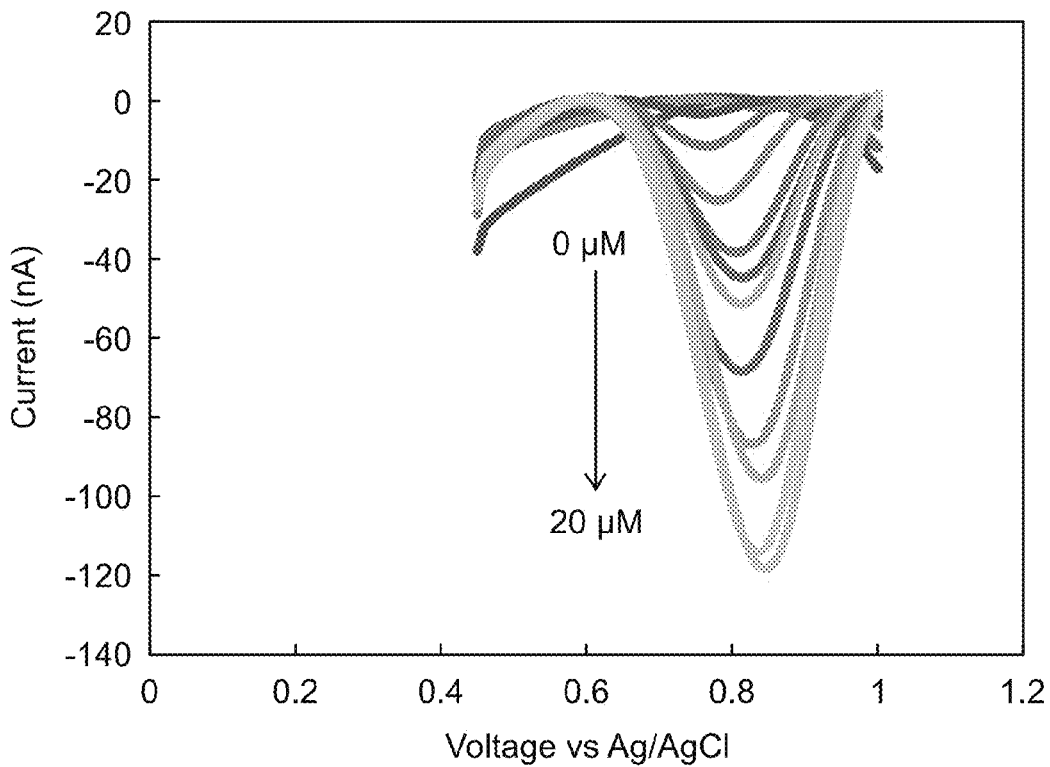
FIG. 11A illustrates differential pulse voltammetry (DPV) of different nitrite concentrations in R-tube EBC bulk.
Figure 11B:
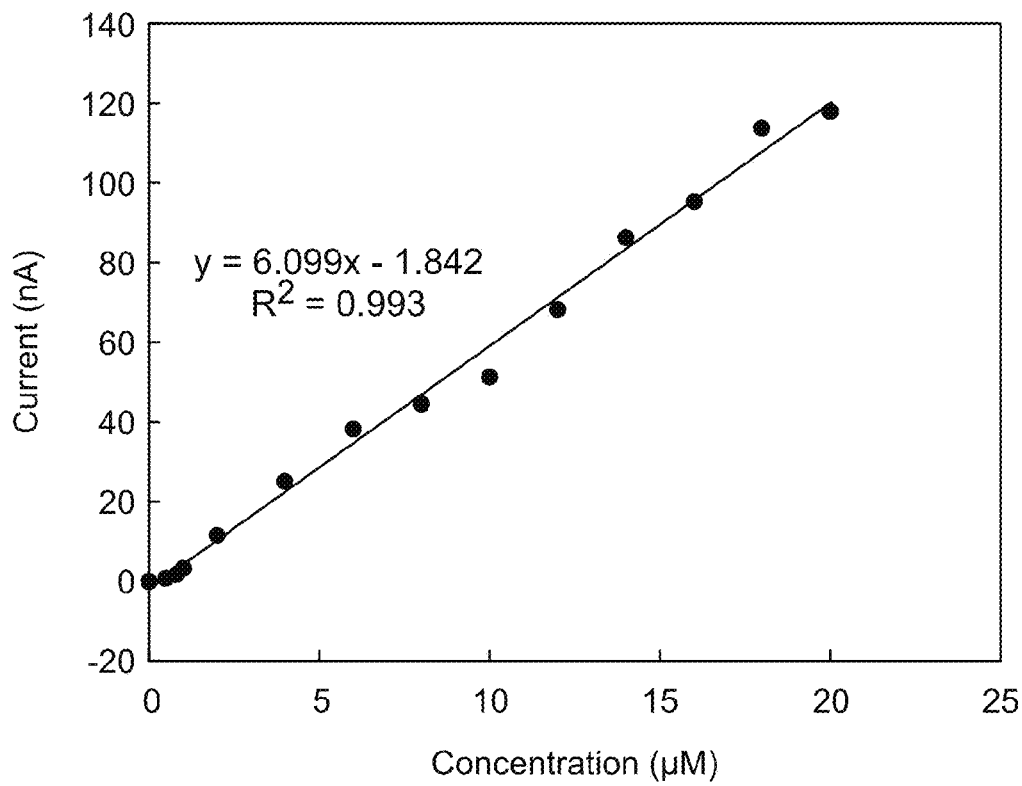
FIGS. 11B-11C illustrate calibration curves obtained from the data in FIG. 11A.
Figure 11C:
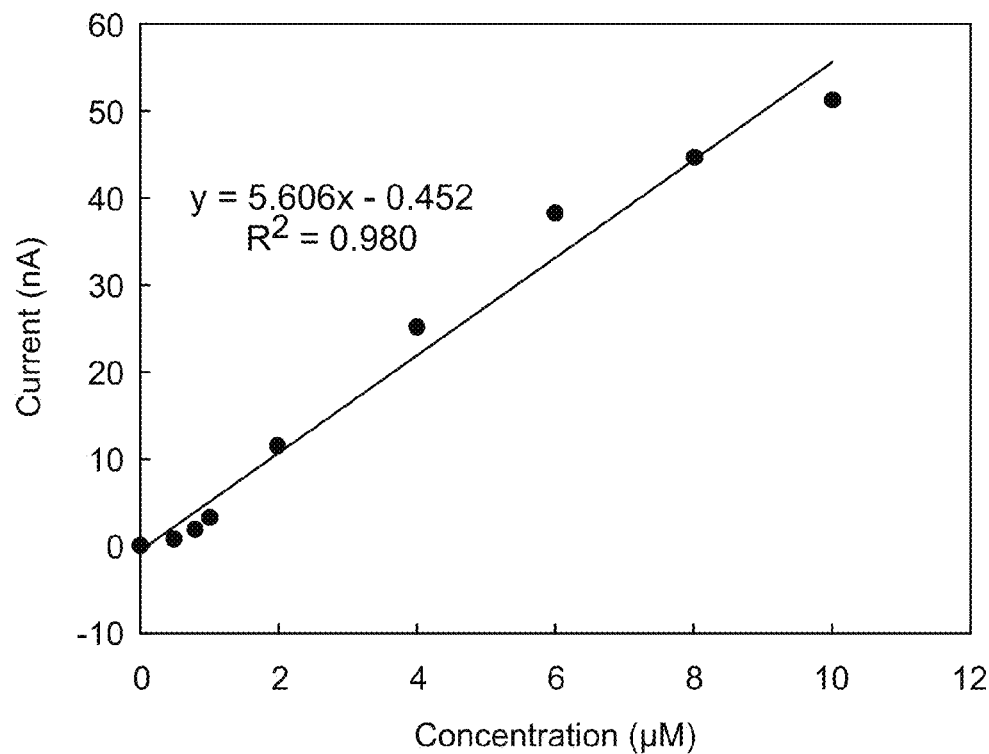
Figure 12A:
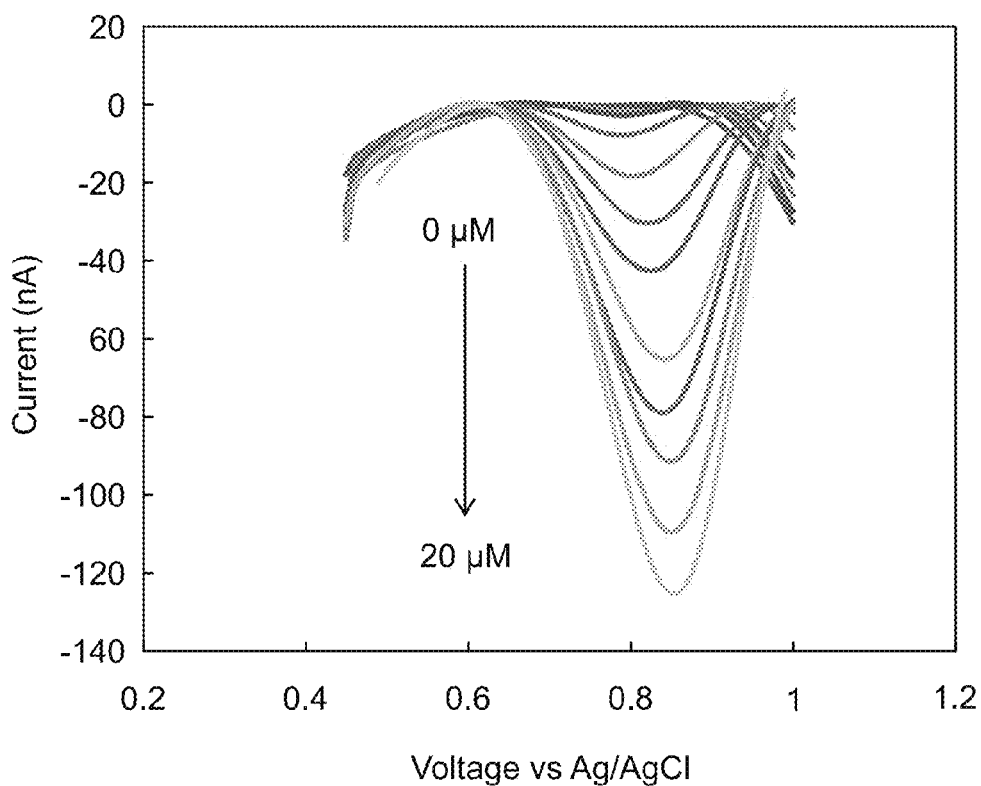
FIG. 12A illustrates differential pulse voltammetry (DPV) of different nitrite concentrations in Eco-screen EBC bulk.
Figure 12B:
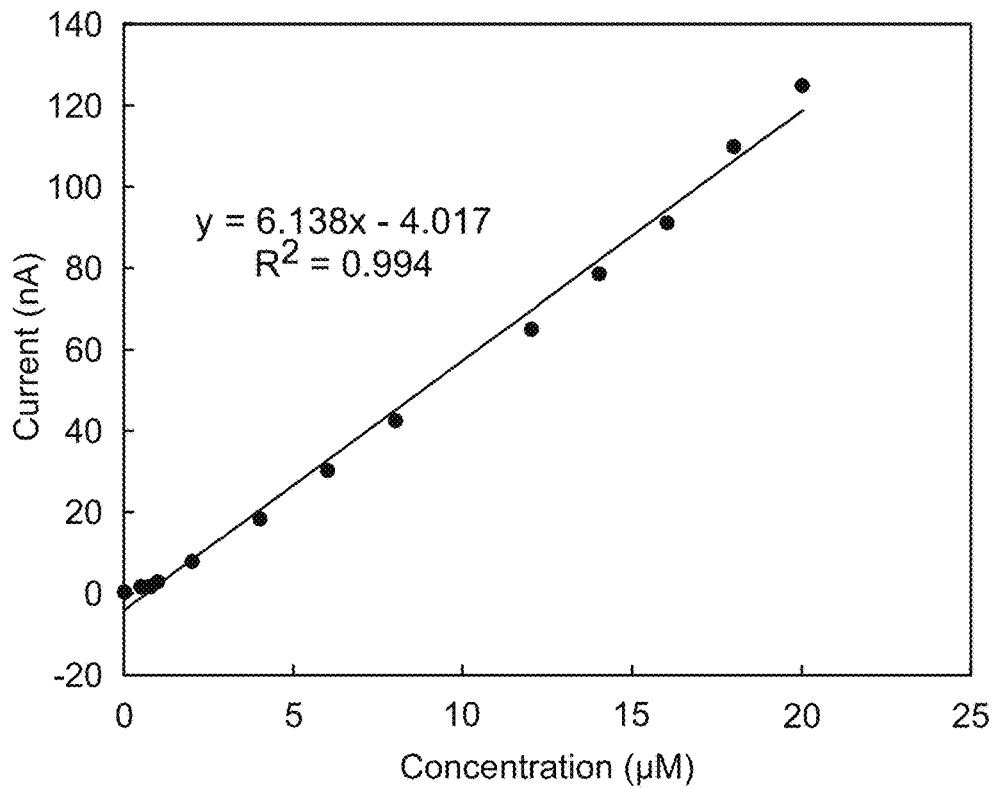
FIGS. 12B-12C illustrate calibration curves obtained from the data in FIG. 12A.
Figure 12C:
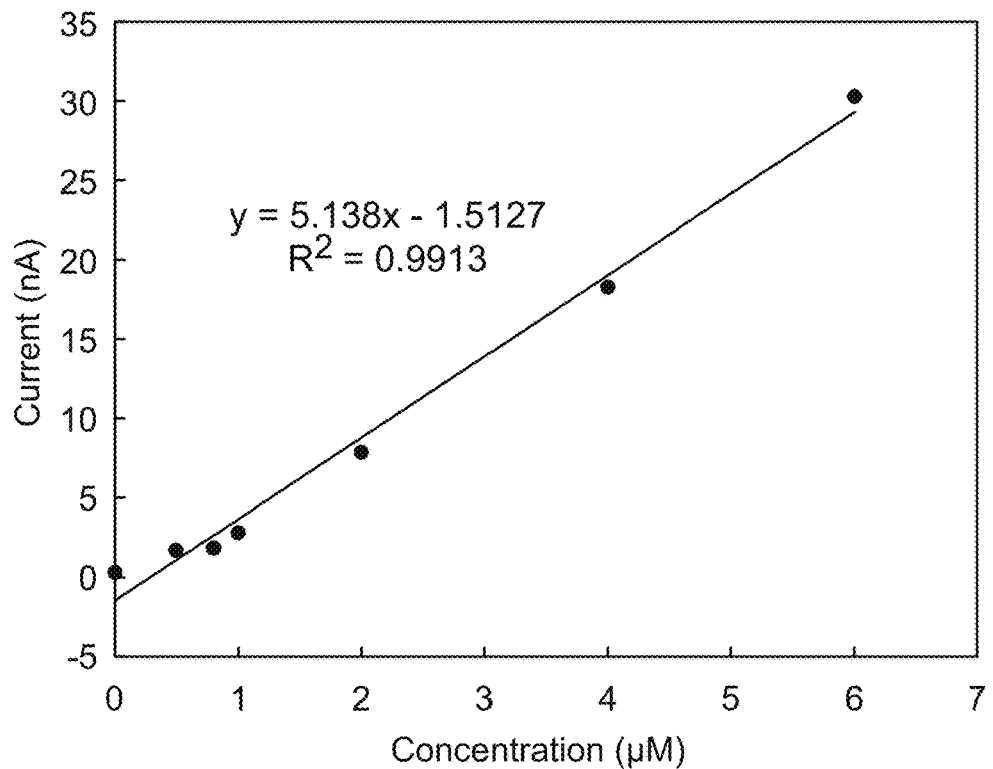

FIGS. 10A-10B show electrochemical performance of sensor in nitrite standard solution. As acetate peaks (curves "a" in FIG. 10A) occur at lower voltages than PBS peaks (curves "b" in FIG. 10A), acetate appears to be a better electrolyte for nitrite detection as compared to PBS. In addition, DPV results show the blank samples that obtained washing R-tube and EcoScreen sampling devices have enough electrical connectivity to be used as electrolytes (FIG. 10B). The DPV and calibration curve of spiked nitrite in EBC blank sample from R-tube and Eco-screen are shown in FIGS. 11A-11C and FIGS. 12A-12C, respectively.

Figure 13A:
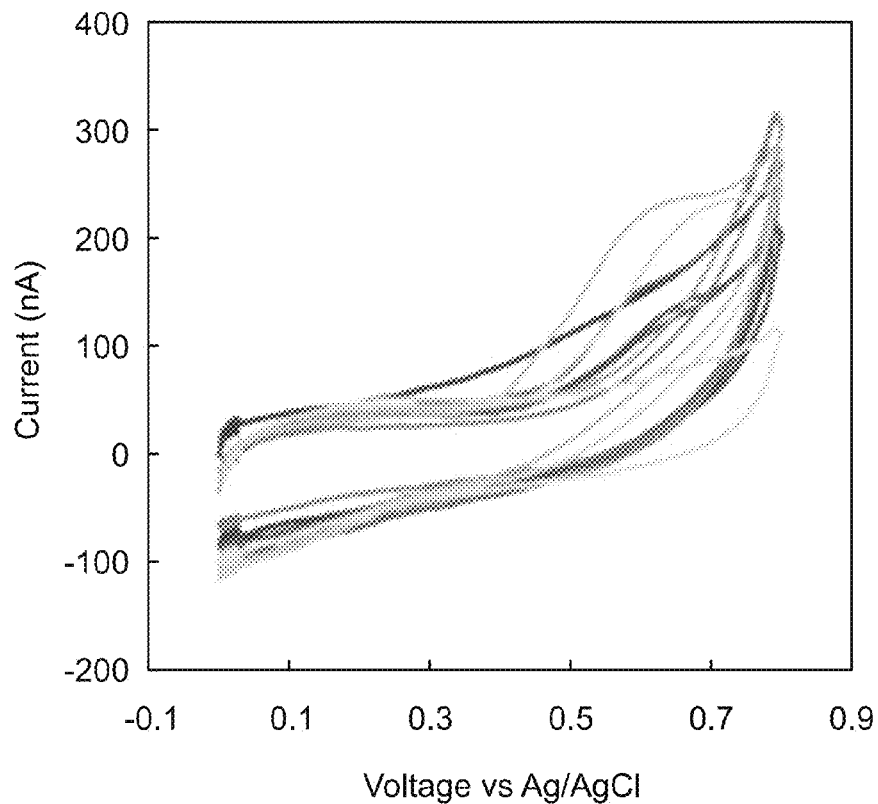
FIG. 13A illustrates cyclic voltammetry (CV) results obtained from fresh samples.
Figure 13B:
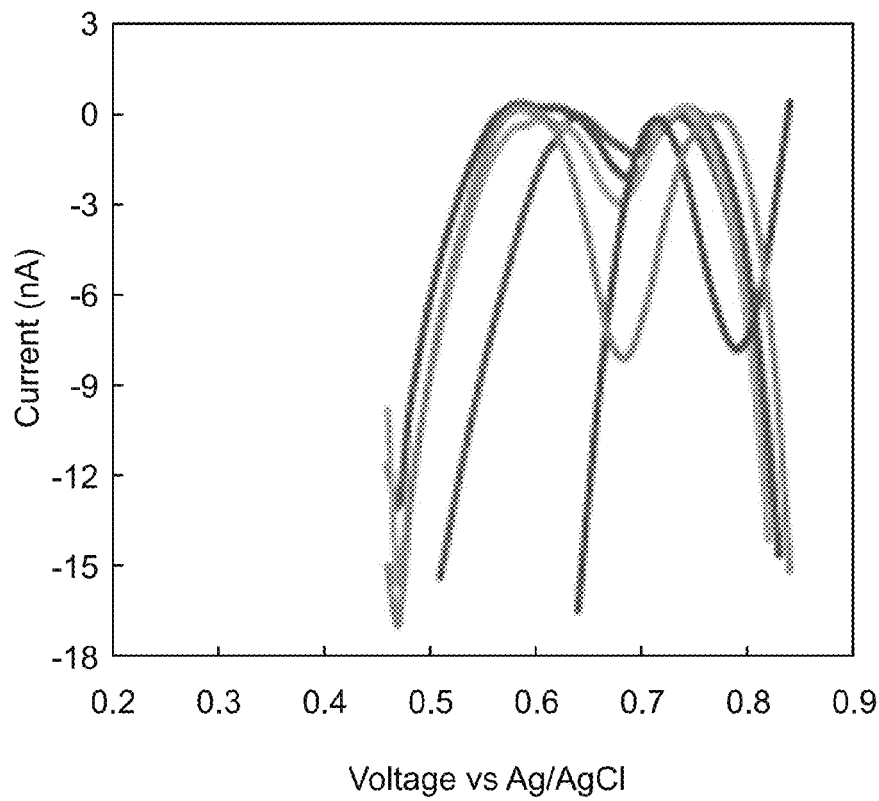
FIG. 13B illustrates DPV results from fresh EBC samples.
Figure 13C:
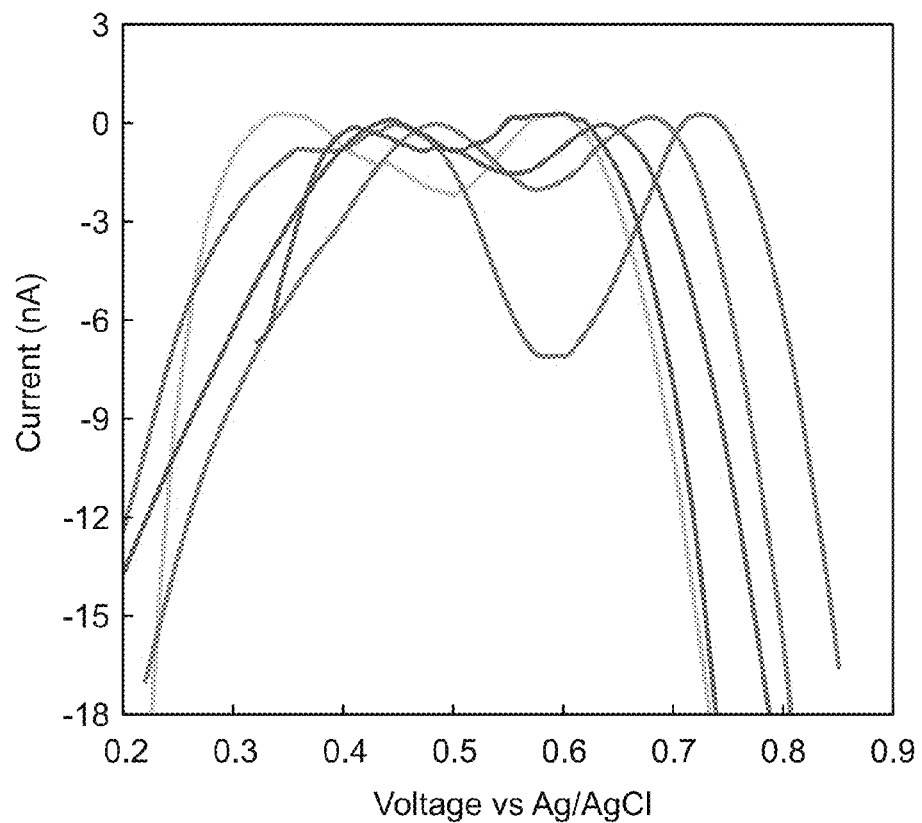
FIG. 13C illustrates DPV results from frozen EBC samples.
Figure 13D:
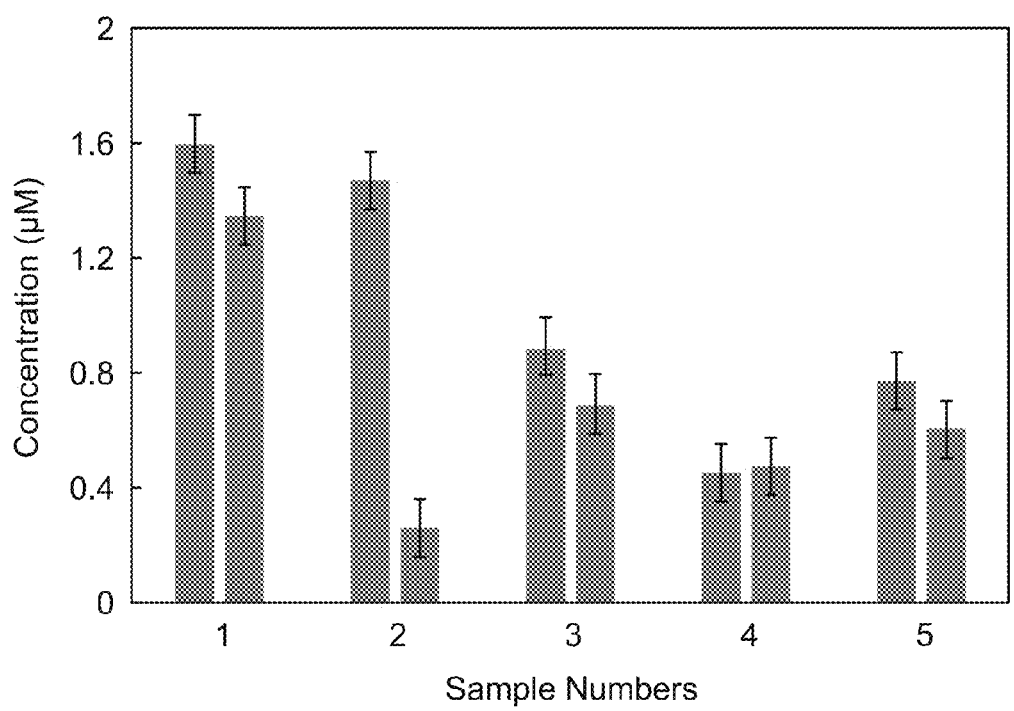
FIG. 13D is a comparison chart of nitrite concentration in fresh and frozen EBC samples.

FIGS. 13A-13D illustrate the results for a case study of fresh and stored EBC samples. FIG. 13A shows CV curves for fresh samples that have been takes from 5 different patients. FIG. 13B shows DVP of the same EBC samples. FIG. 13C shows the DPV results after one month of storage of samples at −80 degrees Celsius. As can be seen in FIG. 13D, for most cases, freezing the samples causes reduction in the amount of nitrite. These results indicate that it is important to measure the nitrite concentration shortly after, and preferably immediately after, collection of sample(s) from the patient. This insight emphasizes the importance of point of care and portable design of biosensors for diagnosis of lung inflammation diseases.

Table 1A (fresh samples) and Table 1B (frozen samples) show the predicted concentration based on R-tube and EcoScreen calibration curves that are reported in FIGS. 11A-11C and FIGS. 12A-12C. The predicted nitrite was calculated based on different sampling methods used for different patients.

TABLE 1A

Predicted level based on different calibration curve: Fresh samples

| Sample | Current (nA) | R-tube. concentration (μM) | EcoScreen. concentration (μM) | acetate. concentration (μM) |
|---|---|---|---|---|
| 1 | 8.575 | 1.6 | 1.96 | 2.07 |
| 2 | 7.79 | 1.47 | 1.81 | 1.92 |
| 3 | 3.08 | 0.63 | 0.89 | 0.96 |
| 4 | 2.08 | 0.45 | 0.7 | 0.76 |
| 5 | 2.375 | 0.5 | 0.77 | 0.82 |

TABLE 1B

Predicted level based on different calibration curve: Frozen samples

| Sample | Current (nA) | R-tube. concentration (μM) | EcoScreen. concentration (μM) | acetate. concentration (μM) |
|---|---|---|---|---|
| 1 | 7.1 | 1.35 | 1.68 | 1.78 |
| 2 | 0.89 | 0.26 | 0.46 | 0.52 |
| 3 | 2.04 | 0.45 | 0.69 | 0.75 |
| 4 | 2.18 | 0.47 | 0.72 | 0.78 |
| 5 | 1.58 | 0.36 | 0.6 | 0.65 |

Figure 14A:
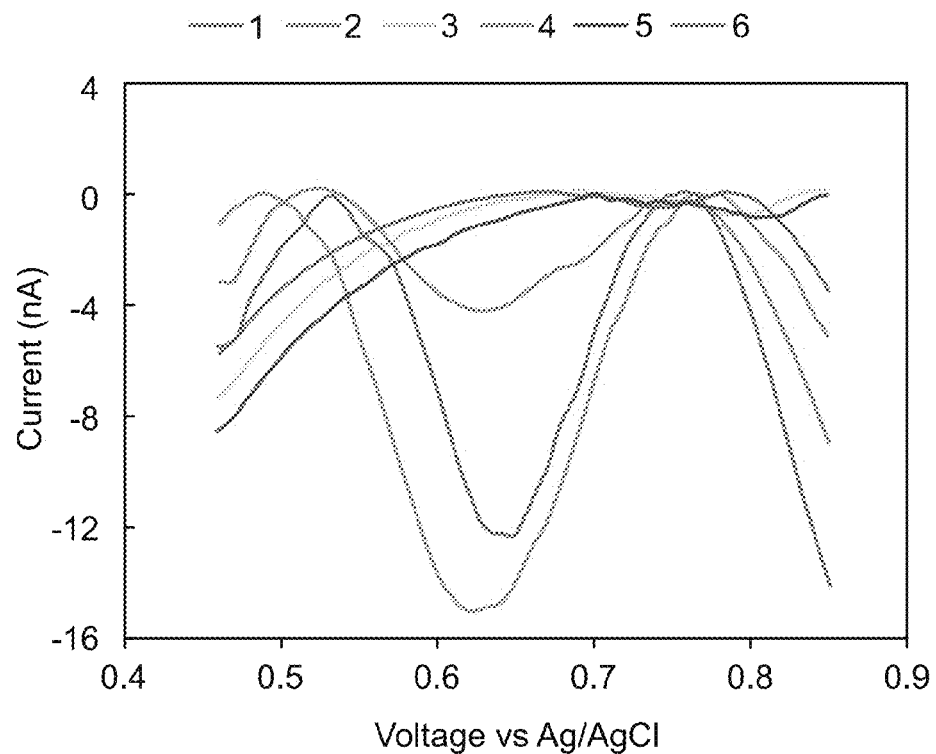
FIG. 14A illustrates DPV results for six EBC samples.
Figure 14B:
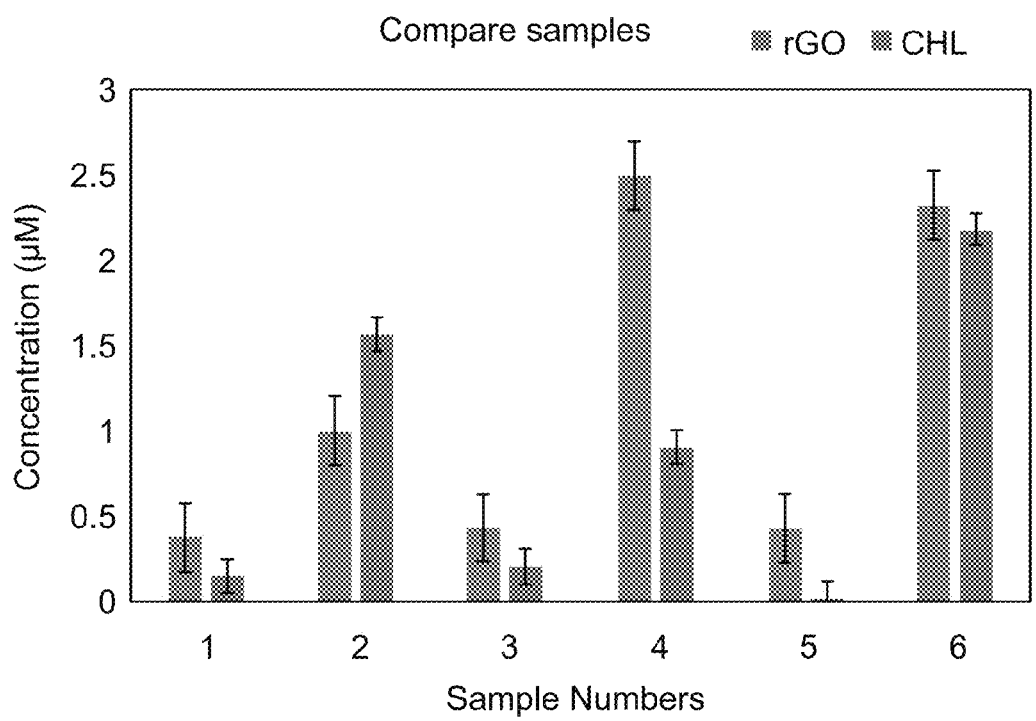
FIG. 14B is a chart comparing predicted concentration using rGO sensor and chemiluminescence for six EBC samples.

FIGS. 14A-14B show data comparing graphene based sensor (rGO) and chemiluminescence (CHL) results of predicted nitrite concentration. These data show good compatibility between the results.

Figure 15A:
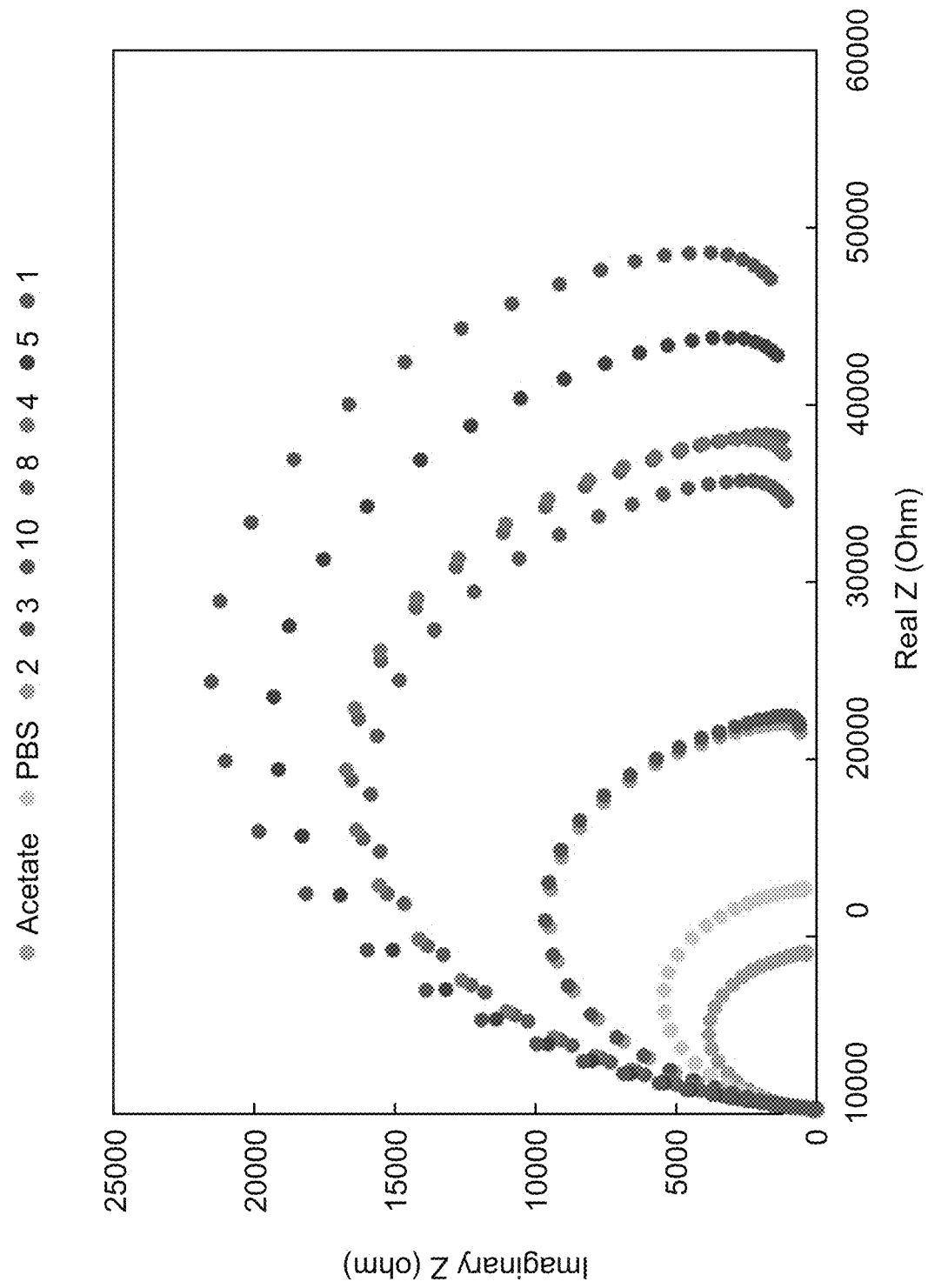
FIG. 15A illustrates electrochemical impedance spectroscopy (EIS) data of EBC samples.
Figure 15B:
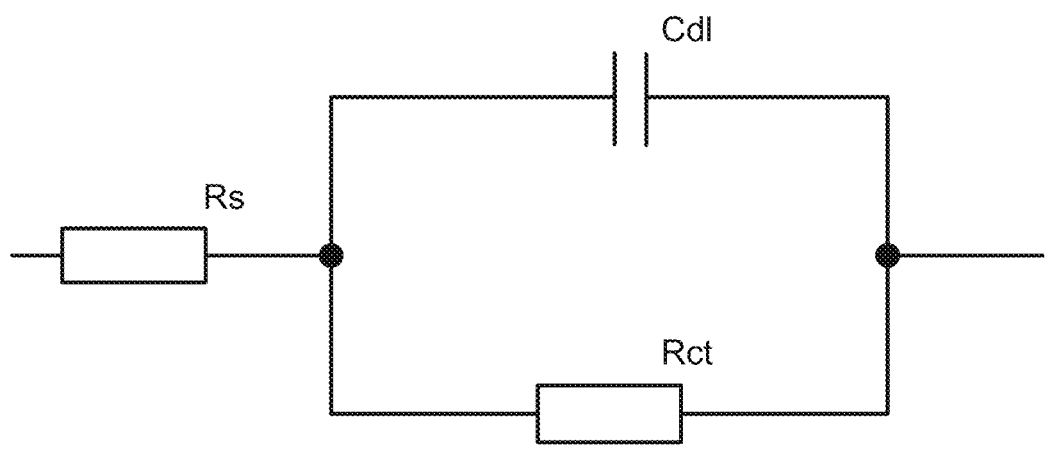
FIG. 15B is a schematic of an equivalent electrical circuit used in the analysis of EIS data of EBC samples. The corresponding circuit parameters are shown in Table 3.

Electrochemical impedance spectroscopy (EIS) is a powerful tool to study electrical properties of the surface and solution. The EIS results of EBC samples are shown in FIG. 15A and their circuit simulation parameters are provided in Table 3. A schematic of an equivalent electrical circuit (e.g., Randles circuit) that was used in the EIS analysis is illustrated in FIG. 15B. Rs represents a solution resistance, Cdl is a double layer capacitance, and Rct is a charge transfer resistance. A Randles circuit is commonly used in EIS for interpretation of impedance spectra. The results indicate the electrical differences between the EBC samples emphasizing that the ionic natures of patient samples are different from each other and that one needs to take this into account in the prediction of nitrite from standard calibration curves.

TABLE 2

Measured pH of EBC samples

| Sample | Type | pH |
|---|---|---|
| 1 | R-tube sample | 7.89 |
| 2 | R-tube sample | 7.64 |
| 3 | EcoScreen sample | 7.67 |
| 4 | R-tube sample | 7.70 |
| 5 | EcoScreen sample | 7.64 |
| 8 | EcoScreen Blank | 7.61 |
| 10 | R-tube Blank | 7.68 |

TABLE 2-continued

Measured pH of EBC samples

| Sample | Type | pH |
|---|---|---|
| Acetate | 0.1M | 6 |
| PBS | 0.1M | 7 |

TABLE 3

Circuit simulation parameters of EBC samples

| Sample | Type | Rct kohm | Rs ohm | Cdl nF |
|---|---|---|---|---|
| 1 | R-tube sample | 49.22 | 279.4 | 748.3 |
| 2 | R-tube sample | 22.08 | 279.2 | 821 |
| 3 | Ecoscreen sample | 22.38 | 275.7 | 762.2 |
| 4 | R-tube sample | 38.4 | 280 | 771.8 |
| 5 | EcoScreen sample | 44.29 | 273.1 | 775.5 |
| 8 | EcoScreen blank | 38.67 | 279.7 | 846.9 |
| 10 | R-tube blank | 36 | 286.4 | 812.3 |
| Acetate | 0.1M | 9 | 200 | 1044 |
| PBS | 0.1M | 12.62 | 188.8 | 780.4 |

Table 2 shows the pH of each of the samples. The results indicate that the pH values of samples are almost the same in the range that can affect electrochemical measurement. Thus, the pH has negligible effect on predicted results.

CONCLUSION

The results reveal the importance of fabrication of a portable biosensor that can detect nitrite amount in fresh samples just after the collection of the samples. In addition, the method of collection samples and electrical properties of EBC samples should be considered in the prediction and reporting of nitrite amount in EBC samples.

REFERENCES

1. Exhaled nitric oxide and biomarkers in exhaled breath condensate indicate the presence, severity and control of childhood asthma. Robroeks et. al. (2007). Clin. Exp. Allergy September; 37(9): 1303-11.
2. Analysis of nitrogen oxide (NOx) in the exhaled breath condensate (EBC) of subjects with asthma as a complement of exhaled nitric oxide (FeNO) measurements: a cross-sectional study. Cherot-Kornobis et. al., (2011) BMC Research Notes 4:202
3. A sensitive and selective nitrite detection in water using graphene/platinum nanocomposite. Vijayaraj et. al. (2017) Eletroanalysis 29:345-351
4. Method for simultaneously detecting ascorbic acid, dopamine, uric acid, tryptophan and nitrite. CN20161239124 (filed Apr. 15, 2016, published Jul. 13, 2016)
5. Nitrite electrochemical sensor and manufacturing method thereof. CN2015146069 (filed Jan. 25, 2015, published May 20, 2015)
6. Electrochemical sensor utilizing nanocomposite comprising reduced graphene oxide and cyclodextrin. KR20160045649 (filed Apr. 14, 2016, published Mar. 8, 2017)

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A device for detecting a biomarker for inflammation in a respiratory system, the device comprising:
    a) a sample collection area to receive an exhaled breath condensate (EBC) sample obtained from a respiratory system;
    b) an electrode system coupled to the sample collection area, the electrode system including reduced graphene oxide (rGO);
    c) circuitry coupled to the electrode system, the circuitry applying a voltage to the EBC sample in the sample collection area via the electrode system and measuring a current via the electrode system in response to the voltage applied, to determine a concentration of nitrite in the EBC sample based on the current measured, the concentration of nitrite being a biomarker for inflammation in the respiratory system.

2. The device of claim 1, wherein the sample collection area and the electrode system form a micro-electrochemical cell defining a small volume area to hold the EBC sample.

3. The device of claim 2, further including a structural layer positioned adjacent the electrode system, the structural layer defining a boundary of the small volume area.

4. The device of claim 3, wherein the structural layer is fabricated from PDMS.

5. The device of claim 1, wherein the electrode system includes a working electrode, a counter electrode, and a reference electrode, the working electrode including the rGO.

6. The device of claim 5, wherein the working electrode, the counter electrode, and the reference electrode are screen printed on a substrate.

7. The device of claim 5, wherein the working electrode is formed using a modified drop cast method, the method including the steps of: depositing a drop of graphene oxide (GO) solution on a surface of a metal electrode, forming the drop of GO into a layer of GO on the surface of the metal electrode, and electrochemically reducing the layer of GO to form a layer of rGO.

8. The device of claim 1, wherein the voltage applied is a time-varying voltage having an amplitude pattern suitable for at least one of cyclic voltammetry, square wave voltammetry, and differential pulse voltammetry.

9. The device of claim 1, wherein the concentration of nitrite in the EBC sample is determined by assessing a peak value in the current measured relative to calibration data.

10. The device of claim 9, wherein the peak value is assessed at a potential of about 0.7 Volts.

11. The device of claim 9, further including a processor in communication with the circuitry and a memory storage, the processor configured to retrieve the calibration data from the memory storage and to calculate the concentration of nitrite based on the current measured and the calibration data retrieved from the memory storage.

12. The device of claim 1, wherein the respiratory system is of a mammalian subject; and the device further includes an output display unit responsive to the determined concentration of nitrite and generating an indication that the subject is asthmatic at threshold concentration levels of the determined concentration of nitrite.

13. The device of claim 1 wherein the EBC sample is one or more of label-free, probe-free, enzyme-free and catalyst-free.

14. A method for detecting a biomarker for inflammation in a respiratory system, the method comprising:
   a) receiving an exhaled breath condensate (EBC) sample in a sample collection area, the EBC sample obtained from a respiratory system;
   b) applying a voltage to the EBC sample via an electrode system coupled to the sample collection area, the electrode system including reduced graphene oxide (rGO);
   c) measuring a current via the electrode system in response to the voltage applied; and
   d) determining a concentration of nitrite in the EBC sample based on the current measured, the concentration of nitrite being a biomarker for inflammation in the respiratory system.

15. The method of claim 14, further including holding the EBC sample in a small volume area of a micro-electrochemical cell formed by the sample collection area and the electrode system.

16. The method of claim 14, wherein the voltage applied is a time-varying voltage having an amplitude pattern suitable for at least one of cyclic voltammetry, square wave voltammetry, and differential pulse voltammetry.

17. The method of claim 14, wherein the concentration of nitrite in the EBC sample is determined by assessing a peak value in the current measured relative to calibration data.

18. The method of claim 17, wherein the peak value is assessed at a potential of about 0.7 Volts.

19. The method of claim 17, further including retrieving the calibration data from a memory storage and calculating the concentration of nitrite based on the current measured and the calibration data retrieved from the memory storage.

20. The method of claim 14, wherein the respiratory system is of a mammalian subject; and further including, responsive to the determined concentration of nitrite, generating an indication that the subject is asthmatic at threshold concentration levels of the determined concentration of nitrite.

* * * * *